(12) United States Patent
Blurton et al.

(10) Patent No.: US 11,202,732 B2
(45) Date of Patent: *Dec. 21, 2021

(54) TISSUE RETENTION SYSTEMS AND METHODS

(71) Applicant: Stetrix, Inc., Oakland, TN (US)

(72) Inventors: David D. Blurton, Whiteville, TN (US); Mark Buchanan, Atoka, TN (US)

(73) Assignee: Stetrix, Inc., Bartlett, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/179,213

(22) Filed: Feb. 18, 2021

(65) Prior Publication Data

US 2021/0169723 A1   Jun. 10, 2021

Related U.S. Application Data

(60) Continuation of application No. 15/977,776, filed on May 11, 2018, now Pat. No. 10,925,792, which is a
(Continued)

(51) Int. Cl.
*A61F 5/37* (2006.01)
*A61B 17/02* (2006.01)
(Continued)

(52) U.S. Cl.
CPC ............ *A61G 13/122* (2013.01); *A61B 17/02* (2013.01); *A61F 5/37* (2013.01); *A61F 5/3776* (2013.01);
(Continued)

(58) Field of Classification Search
CPC ................................................. A41D 13/1169
See application file for complete search history.

(56) References Cited

U.S. PATENT DOCUMENTS

| 572,465 A | 12/1896 | Woolfolk et al. |
| 811,167 A | 1/1906 | Paddock |

(Continued)

FOREIGN PATENT DOCUMENTS

| EP | 1477197 A1 | 11/2004 |
| RU | 2196491 C1 | 1/2003 |

(Continued)

OTHER PUBLICATIONS

Bryant, Ruth A., "Saving the Skin from Tape Injuries", American Journal of Nursing, vol. 88, No. 2, pp. 189-191 (1988).
(Continued)

*Primary Examiner* — Tarla R Patel
(74) *Attorney, Agent, or Firm* — Haynes and Boone, LLP

(57) ABSTRACT

A tissue retention belt for maintaining tissue in a position that permits access to a body portion of a patient for a medical procedure includes a first anchor zone, a second anchor zone, and a tension zone. The tension zone extends between the first anchor zone and the second anchor zone and defines a tension axis that extends in a direction of loading to be applied to retained tissue. The tension zone may include an auxiliary anchor zone that includes a removable non-adhesive and an adhesive surface configured to adhere to a patient's skin and provide auxiliary anchoring for maintaining tissue in position.

19 Claims, 14 Drawing Sheets

Related U.S. Application Data division of application No. 15/645,578, filed on Jul. 10, 2017, now Pat. No. 9,993,382.

(51) Int. Cl.
  *A61G 13/12* (2006.01)
  *A61B 17/00* (2006.01)
(52) U.S. Cl.
  CPC .. *A61F 5/3784* (2013.01); *A61B 2017/00951* (2013.01)

(56) References Cited

U.S. PATENT DOCUMENTS

| | | | |
|---|---|---|---|
| 933,610 | A | 9/1909 | Yanowsky |
| 1,529,937 | A | 3/1925 | Turcotte |
| 1,565,808 | A | 12/1925 | Levy |
| 1,983,636 | A | 12/1934 | Palkens |
| 2,104,699 | A | 1/1938 | O'Dell |
| 2,282,021 | A | 5/1942 | Benningfield |
| 2,327,671 | A | 8/1943 | Rupprecht |
| 2,719,568 | A | 10/1955 | Webb |
| 2,840,822 | A | 7/1958 | Ericsson |
| 3,101,718 | A | 8/1963 | Rocker |
| 3,103,316 | A | 9/1963 | Schaal |
| 3,116,735 | A | 1/1964 | Geimer |
| 3,452,362 | A | 7/1969 | Korolick et al. |
| 3,554,190 | A | 1/1971 | Kaplan |
| 4,239,037 | A | 12/1980 | Fausone |
| 4,530,122 | A | 7/1985 | Sanders et al. |
| 4,615,334 | A | 10/1986 | Jaeger |
| 4,621,619 | A | 11/1986 | Sharpe |
| 4,691,333 | A | 9/1987 | Gabriele et al. |
| 4,706,661 | A | 11/1987 | Barrett |
| 4,732,146 | A | 3/1988 | Fasline et al. |
| 4,782,535 | A | 11/1988 | Yewer, Jr. et al. |
| 4,822,317 | A | 4/1989 | Wimmer |
| 4,825,866 | A | 5/1989 | Pierce |
| 4,866,789 | A | 9/1989 | Dorm |
| 4,981,307 | A | 1/1991 | Walsh |
| 4,995,383 | A | 2/1991 | Anderson |
| 5,007,412 | A | 4/1991 | DeWall |
| 5,040,524 | A | 8/1991 | Votel et al. |
| 5,148,549 | A | 9/1992 | Sydor |
| 5,234,462 | A | 8/1993 | Pavletic |
| 5,432,951 | A | 7/1995 | Yewer, Jr. |
| 5,493,735 | A | 2/1996 | Rice |
| 5,569,165 | A | 10/1996 | Chin et al. |
| 5,690,607 | A | 11/1997 | Chin et al. |
| 5,709,650 | A | 1/1998 | Colman |
| 5,843,025 | A | 12/1998 | Shaari |
| 5,928,059 | A | 7/1999 | Wicks |
| 5,985,395 | A | 11/1999 | Comstock et al. |
| 5,991,979 | A | 11/1999 | Moore et al. |
| 6,071,175 | A | 6/2000 | Working, III |
| 6,123,667 | A | 9/2000 | Poff et al. |
| 6,146,345 | A | 11/2000 | Mignard |
| 6,159,070 | A | 12/2000 | Schwartz et al. |
| 6,572,541 | B1 | 6/2003 | Petersvik |
| 6,623,588 | B1 | 9/2003 | Rasmussen |
| 6,710,099 | B2 | 3/2004 | Cinelli et al. |
| 7,198,609 | B2 | 4/2007 | Rolnick |
| 7,766,931 | B2 | 8/2010 | Blurton |
| 7,776,931 | B2 | 8/2010 | Venter et al. |
| 7,902,420 | B2 | 3/2011 | Kase |
| 8,881,732 | B2 | 11/2014 | Blurton et al. |
| 9,144,423 | B2 | 9/2015 | Blurton et al. |
| 9,205,002 | B2 | 12/2015 | Kase |
| 9,220,627 | B2 | 12/2015 | Fisher |
| 9,408,741 | B2 | 8/2016 | Blurton et al. |
| 9,427,222 | B2 | 8/2016 | Galbierz et al. |
| 9,993,382 | B1 * | 6/2018 | Blurton ............... A61G 13/122 |
| 10,925,792 | B2 * | 2/2021 | Blurton .............. A61B 17/02 |
| 2003/0092969 | A1 | 5/2003 | O'Malley et al. |
| 2004/0067716 | A1 | 4/2004 | Wakefield |
| 2004/0088031 | A1 | 5/2004 | Gomez |
| 2004/0186356 | A1 | 9/2004 | O'Malley et al. |
| 2005/0150503 | A1 | 7/2005 | Votel |
| 2005/0203565 | A1 | 9/2005 | Rethy et al. |
| 2006/0149177 | A1 | 7/2006 | Root et al. |
| 2006/0180158 | A1 | 8/2006 | McKnight et al. |
| 2007/0021779 | A1 | 1/2007 | Garvin et al. |
| 2007/0232864 | A1 | 10/2007 | Sharp et al. |
| 2011/0275969 | A1 | 11/2011 | Quinn |
| 2011/0275983 | A1 | 11/2011 | Quisenberry et al. |
| 2012/0029295 | A1 | 2/2012 | Long Sharps et al. |
| 2013/0133668 | A1 | 5/2013 | Fisher |
| 2016/0100975 | A1 | 4/2016 | Korzelius |
| 2016/0338687 | A1 | 11/2016 | Blurton et al. |

FOREIGN PATENT DOCUMENTS

| | | |
|---|---|---|
| WO | WO 9629013 A1 | 9/1996 |
| WO | WO 9932003 A1 | 7/1999 |
| WO | WO 2006086785 A2 | 8/2006 |
| WO | WO 2007114982 A1 | 10/2007 |

OTHER PUBLICATIONS

Dykes, P.J., "Effects of Adhesive Dressings on the Stratum Corneum of the Skin", Journal of Wound Care, vol. 10, No. 2, pp. 7-10 (2001).

Gerhardt, L.C. et al, "Study of Skin-Fabric Interactions of Relevance to Decubitus: Friction and Contact-Pressure Measurements" Skin Research and Technology, vol. 14, pp. 77-88 (2008).

Goossens, Richard H.M. et al., "Decubitus Risk: Is Shear More Important than Pressure?", Proceedings of the IEA 2000/HFES 2000 Congress, pp. 4-700-4-703 (2000).

Harahap, Marwali, "Surgical Techniques for Cutaneous Scar Revision", pp. 19.

Jacquet, Emmanuelle et al., "A New Experimental Method for Measuring Skin's Natural Tension", Skin Research and Technology, vol. 14, pp. 1-7 (2008).

Karwoski, A.C. et al., "Experiments on Peeling Adhesive Tapes from Human Forearms", Skin Research and Technology, vol. 10, pp. 271-277 (2004).

Koval, Kenneth J. et al., "Tape Blisters following Hip Surgery", Journal of Bone and Joint Surgery, vol. 85-A, No. 10, pp. 1884-1887 (2003).

Lippmann, Maurice et al., "An Alternative Anesthetic Technique for the Morbidly Obese Patient Undergoing Endovascular Repair of an Abdominal Aortic Aneurysm", Anesth. Analg., vol. 97, pp. 981-983 (2003).

Loerakker, Sandra, "Aetiology of Pressure Ulcers", Eindhoven University of Technology, Department of Biomedical Engineering, Section Materials Technology, Division Biomechanics and Tissue Engineering, 31 pgs. (2007).

Murahata, Richard I. et al., "Preliminary Studies on the Relationship among Peel Force, Quantitative Measures of Skin Damage and Subjective Discomfort", Skin Research and Technology, vol. 14, pp. 1-6 (2008).

Ohura, Takehiko et al., "Influence of External Forces (Pressure and Shear Force) on Superficial Layer and Subcutis of Porcine Skin and Effect of Dressing Materials: Are Dressing Materials Beneficial for Reducing Pressure and Shear Force in Tissues?", Wound Repair and Regeneration, vol. 16, pp. 102-107 (2008).

Evren, Sarifakioglu et al., "Dressing Spray Enhances the Adhesive Strength of Surgical Dressing Tapes", Indian Journal of Dermatology, Venerology and Leprology, vol. 72, No. 5, pp. 353-356 (2006).

Thomas, Steve, "Atraumatic Dressings", http://www.worldwidewounds.com/2003/january/Thomas/Atraumatic-Dressings.html, 10 pgs. (2003).

Viegas, Claire M. et al., "Preventing a Surgical Complication During Cesarean Delivery in a Morbidly Obese Patient: A Simple Apparatus to Retract the Abdominal Panniculus", Medscape General Medicine, vol. 8, No. 1, 5 pgs. (2006).

Wang, Qi et al., "In Vivo Biomechanics of the Fingerpad Skin under Local Tangential Traction", Journal of Biomechanics, vol. 40, No. 4, pp. 851-860 (2007).

(56) References Cited

OTHER PUBLICATIONS

Breast Forms, http://www.geocities.com/KarenSpecial/bustform.html, 11 pgs. (Printed Jan. 9, 2008).
Suture Safe®, http://www.canica.com/suturesafe.asp, 2 pgs. (Printed Feb. 14, 2008).
Max-Support™ Abdominal Retraction Belt by Vascular Solutions, Brochure, 4 pgs. (2005).
FLEXcon Providing Solutions in Pressure Sensitive Films, Product Construction Sheet, 1 pg.
3M™ Gamma Stable Medical Fastener, #7333, Gamma Stable Hook Fastener with Adhesive, Preliminary Technical Information Sheet, 2 pgs. (2005).
3M™ Gamma Stable Medical Fastener, #7331, Gamma Stable Loop Fastener with Adhesive, Preliminary Technical Information Sheet, 2 pgs. (2005).
3M Health Care, "Reducing the Risk of Superficial Skin Damage Related to Adhesive Use", 2 pgs. (2005).
Sharp, Brad, "U.S. Appl. No. 60/744,017, filed Mar. 31, 2006", 9 pgs.

* cited by examiner

TISSUE RETENTION SYSTEMS AND METHODS

PRIORITY

This application is a continuation of U.S. application Ser. No. 15/977,776, filed May 11, 2018, now U.S. Pat. No. 10,925,792, which is divisional of U.S. application Ser. No. 15/645,578, filed Jul. 10, 2017, now U.S. Pat. No. 9,993,382, each of which is incorporated herein by reference in its entirety.

TECHNICAL FIELD

This disclosure relates in general to systems and methods for retaining patient body tissue in a desired position and retaining objects in relation to the body tissue. More particularly, in some particular implementations, this disclosure relates to systems and methods for retaining patient body tissue in a displaced position during a medical procedure on a patient.

BACKGROUND

The size and constitution of the human body can affect the availability and efficiency of medical care that can be provided. For example, adipose tissue, such as a pannus or an abdominal apron on an obese patient, may completely obscure access to a body region requiring a medical procedure. In cases of excessive adipose tissue, a treating medical professional attempting to examine, treat or otherwise access the lower abdomen or groin region of the patient may have only limited visualization and may have insufficient access to perform procedures.

Some current systems and methods for dealing with tissue, such as the pannus, include having medical staff use their hands to hold the weight of the pannus or other adipose body tissue during the entire procedure, using tape (or tape in conjunction with spray adhesives) to hold the pannus or other adipose tissue, using hooks that secure or grab the pannus or other adipose tissue, and supporting the pannus or adipose tissue with a sheet that may be tied around the patient's abdomen and to a bed side rail or chair. One example of such known techniques includes the method and apparatus described in U.S. Pat. No. 8,881,732, issued to Blurton et al. on November 2014, entitled "Method and Apparatus for Retention of Adipose Tissue", and assigned to the same assignee as the present disclosure (the '732 patent).

An additional system and method for dealing with tissue includes a sheet-like adhesive film that completely covers the patient's skin in the displaced area. Such a system may have several shortcomings including for example excessive adhesion over the contact area. This may make the adhesive film difficult to apply. In addition, because the film may cover a large area of the body, it may be cumbersome to remove. An example of this type of technique is shown and described in U.S. Pat. No. 9,427,222, issued to Galbierz et al. on Aug. 10, 2016, entitled "Retractor/Stabilizer for Excessive and/or Redundant Tissue and Method of Use", and assigned to GSquared Medical, LLC.

Accordingly, the above-mentioned conventional systems all have shortcomings that continue to make medical procedures difficult. The present disclosure overcomes one or more shortcomings in the art.

SUMMARY

It is an object of the present disclosure to provide a tissue retention belt and method for maintaining tissue in a position that permits access to a body portion of a patient for a medical procedure.

Some examples of the tissue retention belt may include a first anchor zone comprising an adhesive surface configured to adhere to a patient's skin, and may include a second anchor zone spaced from the first anchor zone, the second anchor zone configured to attach to an inanimate object or the patient. A tension zone may be integrated with the first anchor zone and may extend between the first anchor zone and the second anchor zone. The tension zone may define a tension axis that extends in a direction of loading to be applied to retained tissue. The tension zone may include an auxiliary anchor zone that includes a removable non-adhesive outer surface that may cover an adhesive surface configured to adhere to a patient's skin and provide auxiliary anchoring for maintaining tissue in position.

In some aspects, the adhesive surface of the auxiliary anchor zone has a different bond strength than the adhesive surface of the first zone. In some aspects, the first anchor zone, the second anchor zone, and the tension zone are aligned along and intersected by the tension axis. In some aspects, the tension zone comprises a non-adhesive region adjacent the auxiliary anchor zone. In some aspects, the auxiliary anchor zone is disposed adjacent the first anchor zone and between the first and second anchor zones. In some aspects, one of the first anchor zone, second anchor zone, and the tension zone comprises a surgical film. In some aspects, the second anchor zone comprises one of a hook material or a loop material, and the tension zone comprises the other of a hook material or a loop material. The second anchor zone and the tension zone may be selectively attachable about an anchoring structure using hook and loop fastening. In some aspects, the tension zone comprises a plurality of auxiliary anchor zones disposed along the tension zone, each of the plurality of auxiliary anchor zones comprising an independently removable non-adhesive outer surface. In some aspects, the removable non-adhesive outer surface of one of the plurality of the auxiliary anchor zones is separated by perforations from the removable non-adhesive outer surface of another of the plurality of the auxiliary anchor zones. In some aspects, the tension zone is integral with the first anchor zone and affixed to the second anchor zone. In some aspects, the tension zone comprises a patterned adhesive for adhesion to skin of the patient. In some aspects, the patterned adhesive comprises alternating adhesive and non-adhesive portions. In some aspects, the inanimate object is a mechanical structure disposed adjacent to the patient. In some aspects, the first anchor zone is sized to carry a load of at least 5 lbs when adhered to the patient's skin. In some aspects, the first anchor zone, the second anchor zone, and the auxiliary anchor zone comprise a monolithic layer.

Additional examples of the tissue retention belt may include a first anchor zone comprising an adhesive surface configured to adhere to a patient's skin, and may include a tension zone extending from the first anchor zone along a tension axis that extends in a direction of loading to be applied to retained tissue. The tension zone may include an auxiliary anchor zone adjacent the first anchor zone, and auxiliary anchor zone may include a removable non-adhesive outer surface covering an adhesive surface configured to adhere to a patient's skin. A second anchor zone may extend from the tension zone and be disposed at a location spaced along the tension zone apart from the first anchor zone and apart from the auxiliary anchor zone.

In some aspects, the tension zone comprises a non-adhesive portion adjacent the auxiliary anchor zone, the non-adhesive portion being arranged to contact the patient's skin. In some aspects, the first anchor zone and the tension zone comprise a monolithic layer. In some aspects, the first anchor zone is an adhesive pad configured to adhere to a patient's skin and the tension zone is selectively attachable to the adhesive pad. In some aspects, the second anchor zone is an adhesive pad configured to adhere to a patient's skin and the tension zone is selectively attachable to the second anchor zone. In some aspects, the first anchor zone, the second anchor zone, and the tension zone are all aligned and intersected by the tension axis. In some aspects, the adhesive surface of the auxiliary anchor zone has a lower bond strength than the adhesive surface of the first zone. In some aspects, the tension zone comprises a non-adhesive region adjacent the auxiliary anchor zone and disposed between the auxiliary anchor zone and the second anchor zone. In some aspects, the second anchor zone comprises one of a hook material or a loop material and the tension zone comprises the other of a hook material or a loop material, the second anchor zone and the tension zone being selectively attachable about an anchoring structure using hook and loop fastening. In some aspects, the tension zone comprises a plurality of auxiliary anchor zones disposed along the tension zone, each of the plurality of auxiliary anchor zones comprising a removable non-adhesive outer surface.

Some examples of methods may include providing a tissue retention belt as described herein, exposing the adhesive surface of the first anchor zone by removing a backing material, and adhesively adhering the first anchor zone to a patient's skin at a first skin location and attaching the second anchor zone at an anchor location spaced apart from the first skin location. The first and second anchor zones may be tautly connected via the tension zone along a tension axis that extends in a direction of applied loading.

The method also may include exposing the adhesive surface of the auxiliary anchor zone by removing the non-adhesive outer surface of the auxiliary anchor zone and adhesively adhering the adhesive surface of the auxiliary anchor zone to the patient to distribute skin loading onto both the first anchor zone and the auxiliary anchor zone. The method also may include revising the fit of the tissue retention belt by unattaching the second anchor zone prior to exposing the adhesive of the auxiliary anchor zone and after adhesively adhering the auxiliary anchor zone, reattaching the second anchor zone. The method also may include exposing the adhesive of the auxiliary anchor zone and adhesively adhering the auxiliary anchor zone prior to attaching the second anchor zone at the anchor location spaced apart from the first skin location. The method also may include looping the second anchor zone around a physical structure and attaching the second anchor zone to itself.

Further objects, forms, implementations, aspects, features, benefits, and advantages of the present disclosure shall become apparent from the detailed drawings and descriptions provided herein.

DETAILED DESCRIPTION

Figure 1:
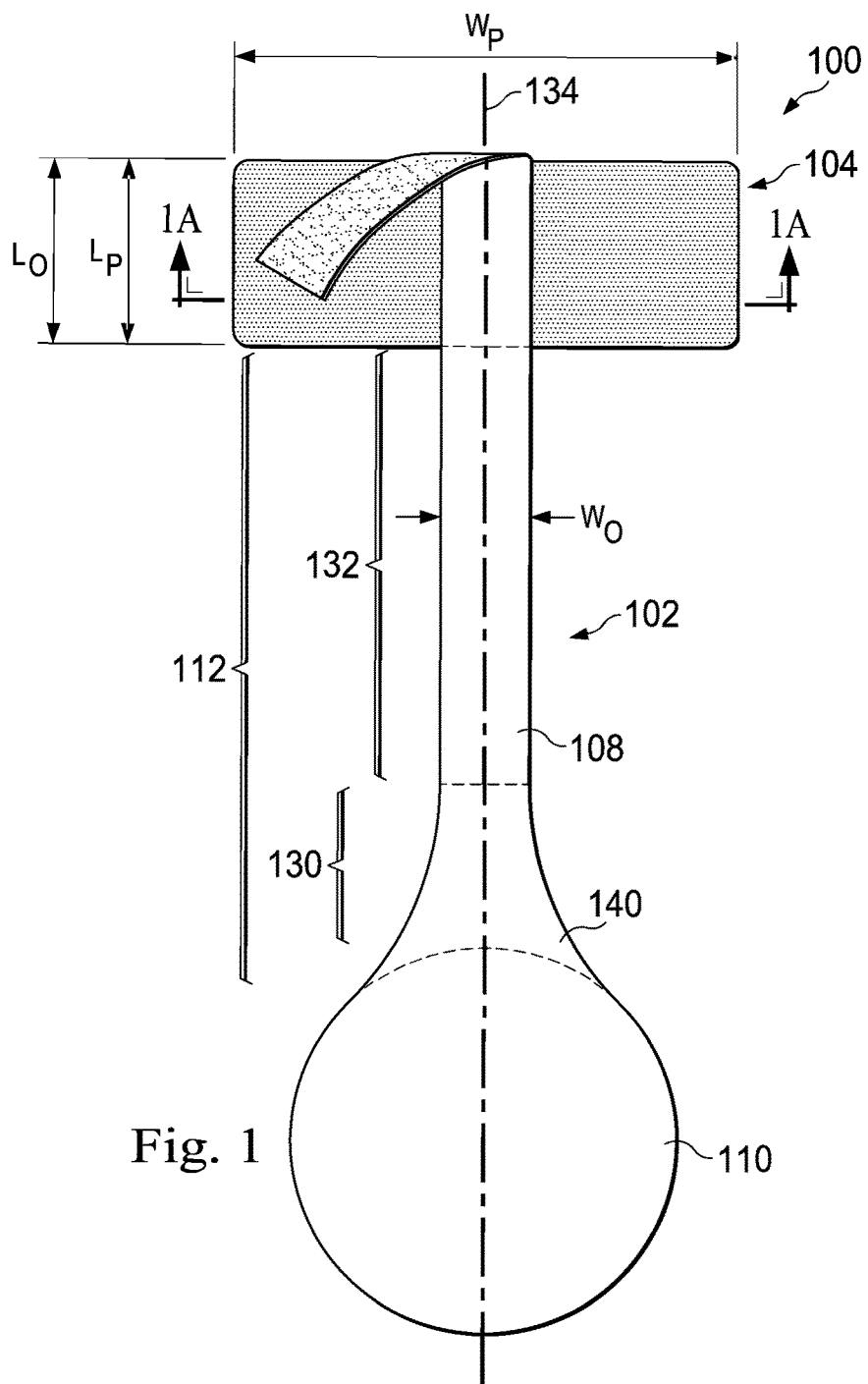
FIG. 1 is an illustration of an exemplary tissue retention system according to an exemplary implementation of the present disclosure.

For the purposes of promoting an understanding of the principles of the invention, reference will now be made to certain implementations, or examples, illustrated in the drawings and specific language will be used to describe the same. It will nevertheless be understood that no limitation of the scope of the invention is thereby intended. Any alterations and further modifications in the described implementations, and any further applications of the principles of the invention as described herein are contemplated as would normally occur to one skilled in the art to which the invention relates.

Adipose tissue may hinder access to regions of the patient's body during routine or non-routine healthcare treatment. For example, in some instances, adipose tissue may detrimentally affect visualization or other access to regions of the patient's body to perform procedures, such as, for example, panniculectomies, to treat panniculitis, general wound care, femoral catheterization, tracheal intubation, cesarean sections, hysterectomies, among other medical procedures.

The tissue retention system disclosed herein includes a tissue retention belt that may be used to maintain adipose tissue in a position that provides better access to patient body regions requiring treatment. For example, it may be used to displace or secure adipose tissue, such as the abdominal apron or pannus, out of the lower abdomen or groin region during child birthing to provide better visualization and easier access to an attending health care provider.

Skin is composed of multiple layers. The main layers comprise the epidermis layer, the dermis layer, and subcutaneous tissue. The epidermis layer comprises sublayers including stratum corneum, stratum ludidum (not present in thin skin, only thick, hairless skin of palms & soles), stratum granulosum, stratum spinosum, and stratum germinativum. The tissue retention system disclosed herein is a non-penetrating solution that adheres to the epidermal layers of the skin without adhering to the dermis or subcutaneous tissue to displace adipose tissue. Further, certain aspects do so without penetrating or pinching tissue to obtain skin anchorage, unlike hooks or other skin gripping systems, which can damage the skin. Instead, it is flexible enough to conform to natural curves of the anatomy, without major tissue deformation or penetration. It may be desirable to employ a tissue retention system having one or more auxiliary anchor zones that permits a healthcare provider to customize the adhesion area of the belt to the patient. Doing so may allow the health care provider to avoid excessive over adhesion, while still providing sufficient adhesion to safely and properly maintain the tissue in a desired position. Excessive over adhesion may make separation of the tissue retention belt from the skin tedious, painful and cumbersome. Excessive under adhesion may result in overly heavy loads across small skin areas, resulting in damage to the skin or delamination of skin layers.

While the emphasis of this discussion is on retention of the pannus for child birthing, it is noted that the present tissue retention system has application in displacing or maintaining adipose tissue of other body regions for many different medical applications, only some of which are discussed herein. Alternative uses may be shown in the '732 patent, which is incorporated herein in its entirety. Further, while movement and retention of adipose tissue is illustrated for surgical access, it will be appreciated that adipose tissue may be mobilized for other reasons, such as, for example, restraining tissue (offloading weight) on the chest area that inhibits breathing in some patient positions.

Turning now to FIGS. 1, 1A, 2, 3, and 3A, the tissue retention system, referenced herein by the numeral 100, includes a tissue retention belt 102 and a separable anchor pad 104. As discussed in greater detail below, the tissue retention belt 102 is configured to attach directly to a patient's skin, such as adjacent adipose tissue. The tissue retention belt 102 includes a facing body side 106 and an opposing facing away side 108. In use, the facing body side 106 is in contact with the patient. The tissue retention belt 102 also includes a primary anchor zone 110 at a distal region, a tension zone 112, and a secondary anchor zone 114 at a proximal region.

As used herein, the "primary anchor zone" refers to an anchor attachable to adjacent adipose tissue, and the "secondary anchor zone" refers to an anchor attachable at a location spaced apart from the primary anchor zone. As will become apparent from the disclosure herein, the secondary anchor zone may be attachable to the anchor pad 104, patient's skin, a mechanical structure or other inanimate object such as a portion of the surgical bed, additional portions of the tension zone 112, or other locations.

Figure 1A:
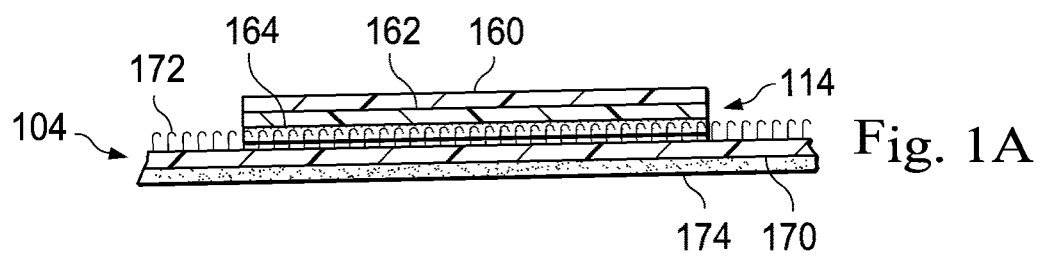
FIG. 1A is an illustration of a cross-sectional view taken along lines 1A-1A in FIG. 1 of the exemplary tissue retention system according to an exemplary implementation.
Figure 2:
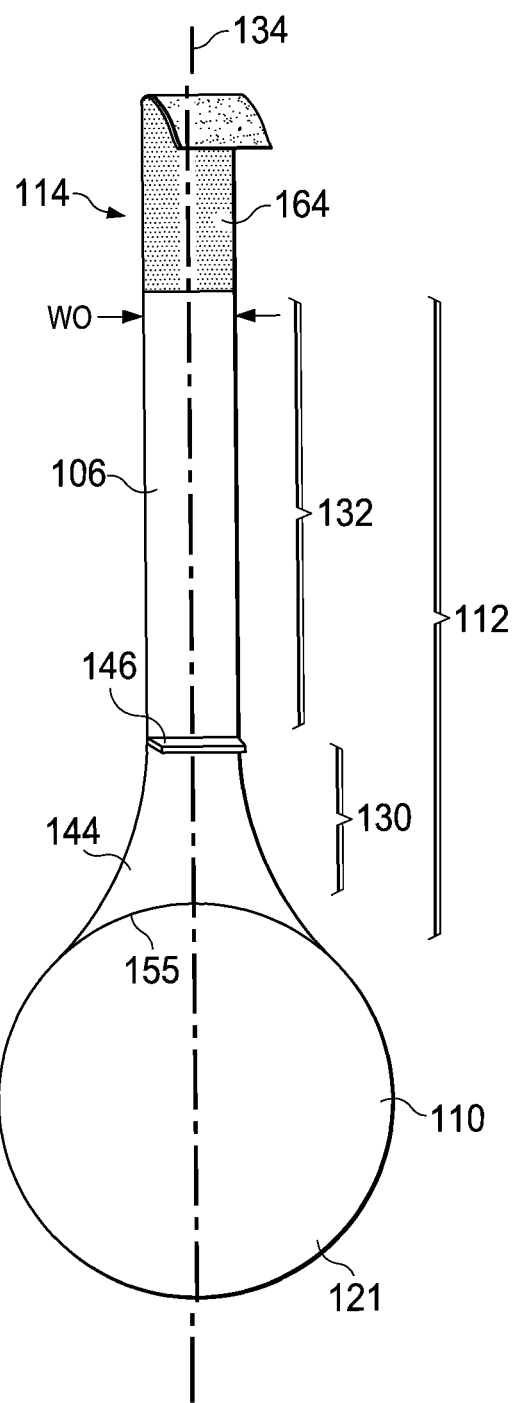
FIG. 2 is an illustration of an exemplary tissue retention belt of the tissue retention system having an auxiliary anchor zone according to an exemplary implementation of the present disclosure.
Figure 3A:
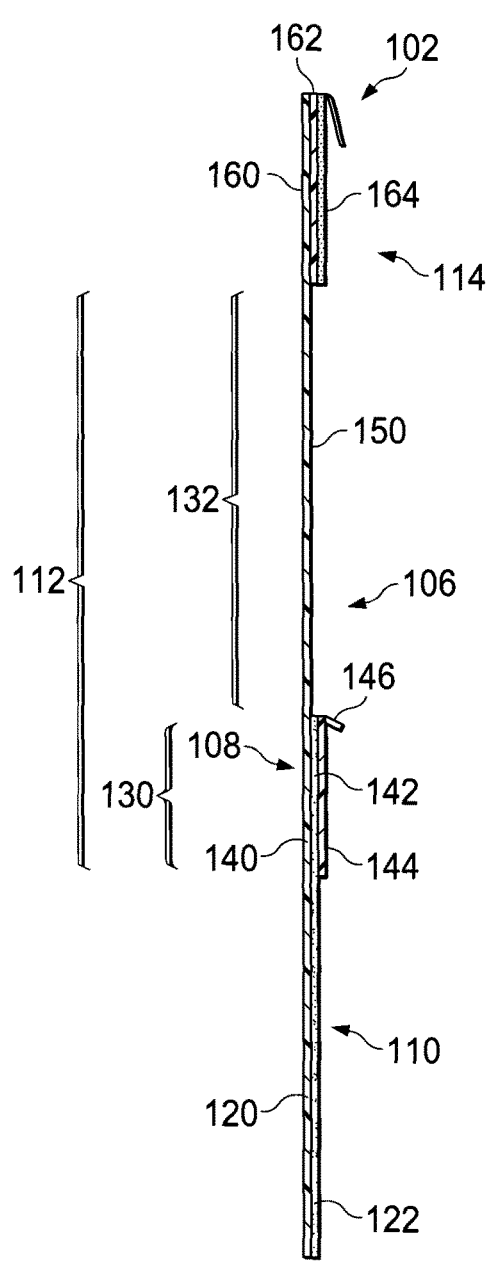
FIG. 3A is an illustration of a cross-sectional view taken along lines 3A-3A in FIG. 3 of the exemplary tissue retention belt according to an exemplary implementation.
Figure 3:
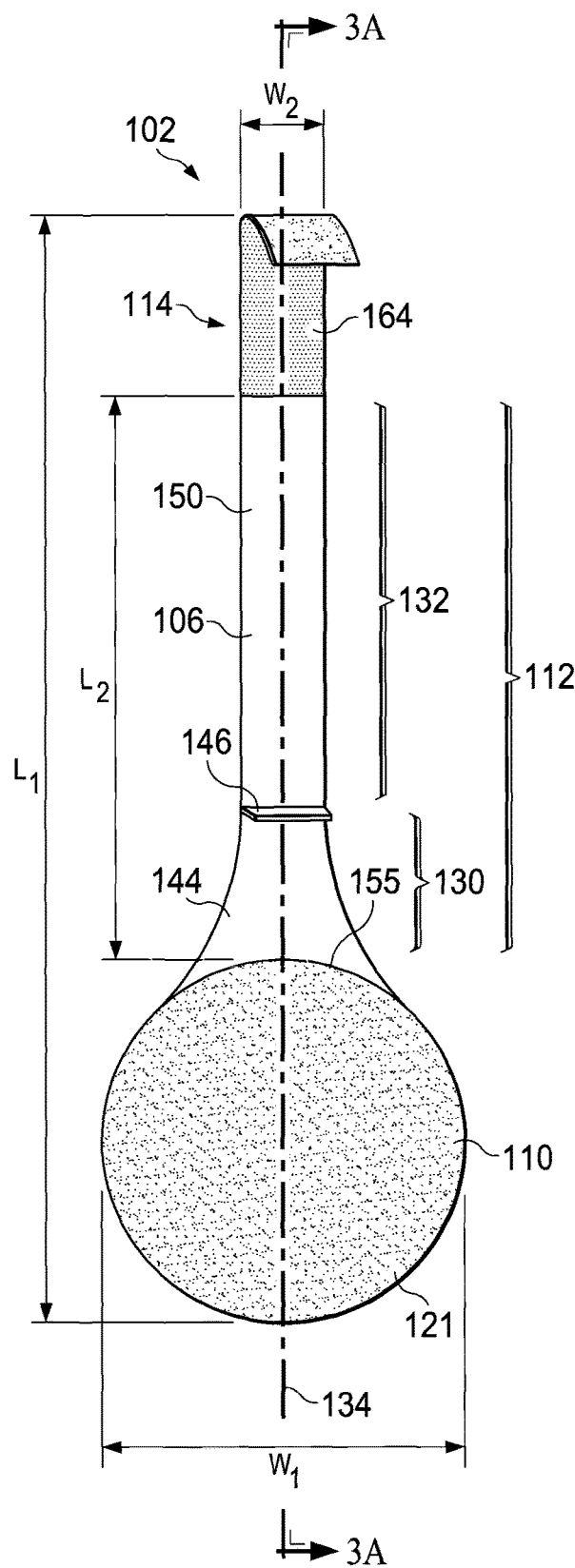
FIG. 3 is an illustration of an exemplary tissue retention belt of the tissue retention system having an exposed adhesive layer according to an exemplary implementation of the present disclosure.

FIG. 1 shows a top view of the tissue retention system 100; FIG. 1A shows a cross-sectional view of the tissue retention system 100 taken along lines 1A-1A in FIG. 1; FIG. 2 shows a bottom view of the tissue retention belt 102 with a removable backing; FIG. 3 shows a bottom view of the tissue retention belt 102 without a portion of the removable backing; FIG. 3A shows a cross-sectional view of the tissue retention belt 102 taken along lines 3A-3A in FIG. 3.

In the implementation shown, and as best shown in FIGS. 3 and 3A, the primary anchor zone 110 of the tissue retention belt 102 includes a body portion 120 which serves as a stabilizing backing for a biocompatible adhesive layer 122. The body portion 120 may be a film, a fabric, a woven material, a mesh material, a matting, paper, a polymer such as a plastic, or any flexible yet suitable material. The adhesive layer 122 is configured to adhere directly to a patient's skin or an inanimate surface. Some implementations are formed of a polyurethane film with a polyacrylate adhesive. In some implementations, the adhesive of the adhesive layer 122 is configured to easily release from the patient's skin with minimal damage or soreness after a medical procedure is complete. In some implementations, prior to use, the adhesive layer 122 faces a non-stick removable backing 121 (FIG. 2) that can be peeled away to reveal the adhesive layer 122 on the body portion 120. FIG. 2 shows the tissue retention belt 102 with the removable backing 121 in place, and FIGS. 3 and 3A show the tissue retention belt 102 without the removable backing in place. The removable backing 121 is a protective layer that covers the adhesive layer 122 of the primary anchor zone 110. The removable backing 121 may be any material, such as a non-stick plastic material, that may be left attached to the adhesive layer 122 to prevent the adhesive layer 122 from coming inadvertently into contact with or adhering to the patient's body. The removable backing 121 may be configured to be cut or sliced, punctured, perforated, or penetrated with an instrument or device. The adhesive layer 122 may be formed of a biocompatible adhesive that may secure the primary anchor zone 110 to the patient's skin. Examples of suitable adhesives include, without limitation, acrylic adhesives, silicone based adhesives, urethane adhesives, synthetic or natural rubber adhesives, among others.

The tension zone 112 extends from a location directly adjacent the primary anchor zone 110. In this implementation, the tension zone 112 extends the full distance between the primary anchor zone 110 and the secondary anchor zone 114. With reference to FIG. 3, the tension zone 112 includes an auxiliary anchor zone 130 and a non-adhering contact region 132. The tension zone 112 defines tension axis 134. Since the tension zone 112 is disposed between the primary anchor zone 110 and the secondary anchor zone 114, the tension axis 134 extends between and also intersects the primary anchor zone 110 and the secondary anchor zone 114. As will become apparent by this disclosure, the tension axis 134 extends in a direction of loading to be applied to retained tissue.

The auxiliary anchor zone 130 includes a body portion 140 and an adhesive layer 142. In addition, the auxiliary anchor zone 130 includes a removable backing 144. In some implementations, the body portion 140 may be integral with and an extension of the body portion 120 from the primary anchor zone 110, thereby forming a monolithic layer. In other implementations, the body portion 140 may be permanently affixed to the body portion 120. For example, the body portion 140 and the body portion 120 may be permanently affixed by being sewn together, welded together, glued to each other, or otherwise connected in a way that makes them unseparable. In a similar manner, the adhesive layer 142 of the tension zone 112 may be a continuous extension from the adhesive layer 122 of the primary anchor zone 110. In other implementations, the adhesive layers 122, 142, are substantially adjacent to each other and may be of differing adhesive strength so that they each support each other during various loading situations to distribute any applied load over both the primary anchor zone 110 and the auxiliary anchor zone 130. In the implementation shown, the removable backing 144 is a protective layer that covers the adhesive layer 142 of the auxiliary anchor zone 130. It may be formed of the material described above with reference to removable backing 121. When needed, the removable backing 144 may be configured to be removed from the adhesive layer 142 to expose the adhesive layer 142 so that it can contact and adhere to the patient's skin. Accordingly, the removable backing 144 may be utilized by a healthcare provider to customize the size of the adhesive area of the tissue retention belt 102. The removable backing 144 may be formed of a biocompatible backing material utilized in the medical industry.

In the exemplary embodiment shown, the removable backing 144 includes a graspable tab 146 that extends from an edge of the adhesive layer 142. The graspable tab 146 is attached to the removable backing 144 in a manner enabling the health care provider to remove the removable backing 144 from the adhesive layer 142 by pulling the graspable tab 146. In some implementations, the graspable tab 146 may simply be an extension of the removable backing 144. In the implementation shown, the graspable tab 146 is disposed at a location of the auxiliary anchor zone 130 closest to the secondary anchor zone 114. However, the graspable tab 146 may be disposed at any point about the auxiliary anchor zone that enables a healthcare provider to remove the removable backing 144 from the auxiliary anchor zone 130.

The non-adhering contact region 132 of the tension zone 112 extends between the auxiliary anchor zone 130 and the secondary anchor zone 114. This portion of the tension zone 112 may be formed to not adhere to the patient's body. Accordingly, even when the auxiliary anchor zone 130 is used to adhere to a patient, the non-adhering contact region 132 provides a nonstick zone that allows adjustment, pulling, and shifting of the proximal end and the secondary anchor zone 114 of the tissue retention belt 102. In some implementations, the non-adhering contact region 132 is formed as a skin contact area that may include for example a layer of hook material or loop material, an adhesive backer, or in some implementations, no adhesive at all.

FIG. 3A shows a cross-sectional view of the non-adhering contact region 132. In the implementation shown, the non-adhering contact region 132 is formed of a body portion 150 that extends from the auxiliary anchor zone 130 toward the secondary anchor zone 114. In the exemplary embodiment shown, the body portion 150 may be integral with an extension of the body portion 140 that forms a part of the auxiliary anchor zone 130, thereby forming a monolithic layer therewith. In some implementations, the body portion 150 may be integral with and an extension of the body portions 120 and 140, thereby forming a monolithic layer therewith. In other implementations, the body portion 150 may be permanently affixed to the auxiliary anchor zone by using any of the example methods described herein including, without limitation, sewing, ultrasonic welding, adhering, and others.

The non-adhering contact region 132 in the implementation shown is an adhesion free zone. In other implementations, the non-adhering contact region 132 may be covered with one or more alternative layers of material. For example, some implementations may include a layer of hook or loop material along the non-adhering contact region. This may include a loop material with soft fiber loops that are gentle on the skin. Other implementations include an adhesive layer that is covered in a manner preventing the adhesive layer from contacting the skin of the patient. Some implementations include an adhesive backer covering an adhesive layer in the non-adhering contact region 132.

The secondary anchor zone 114 is disposed at the proximal end of the tissue retention belt 102. The secondary anchor zone 114 may be arranged to adhere to the anchor pad 104 in FIG. 1 or adhere to another surface about the patient. In some examples, the secondary anchor zone 114 may be located to attach to a mechanical structure or other inanimate object, such as a bedframe, a bed rail, or other anchor location. In some examples, the secondary anchor zone 114 may be located to attach to the patient itself.

With reference to FIG. 3A, the secondary anchor zone 114 is fixedly attached directly adjacent the non-adhering contact region 132. In some implementations, the secondary anchor zone 114 may include one or more layers of material integrally formed with the tension zone 112 and/or the primary anchor zone 110, such that one or more monolithic layers form a part of at least the secondary anchor zone 114 and the tension zone. In this implementation, the secondary anchor zone 114 includes a body portion 160, an attachment surface 162, and a fastening feature 164 formed on the attachment surface 162. Here the fastening feature 164 is a plurality of generally soft fiber loops on the attachment surface 162. In some examples, the fastening feature 164 is a hook material instead of a loop material. Other implementations have different fastening features. As will be described herein, some implementations employ an adhesive layer that makes up the attachment surface 162 and the fastening feature 164. The adhesive layer may attach to the separable anchor pad 104 of FIG. 1. In some implementations, the fastening feature 164, whether a hook, loop, adhesive, or other material, is included over substantially the entire attachment surface 162 of the secondary anchor zone 114. Although many types of materials may be used, in an example, the body portion 160 may be formed of a polyethylene material and the attachment surface 162 may be formed of a nylon material. In the exemplary embodiment shown, the body portion 160 may be integral with an extension of the body portion 150 forming a part of the tension zone 116, thereby forming a monolithic layer therewith. In some implementations, the body portion 160 may be integral with and an extension of the body portions 120, 140, and 150, thereby forming a monolithic layer therewith.

The tissue retention belt 102 is at least partially flexible and configured to conform to contours of the patient's body shape. For example, the tissue retention belt 102 may be sufficiently flexible to conform about a patient's curved abdominal apron or along a patient's curved thigh or conform to other portions of a patient's body. In an exemplary embodiment, tissue retention belt 102 is fully flexible over its overall length.

In FIGS. 2 and 3, a cut 155 in the backing material separates the removable backing 121 from the removable backing 144. The cut 155 may be a die cut that enables a health care provider to expose the adhesive layer 122 of the primary anchor zone 110 without exposing the auxiliary anchor zone 130. In some implementations, the cut 155 extends completely through the removable backing layer and the adhesive layer. In other implementations, the cut 155 is a line of perforations. In such an implementation, the health care provider may tear along the perforations to remove the removable backing material 121 from the primary anchor zone 110 without removing the backing material 144 of the auxiliary anchor zone 130.

In the implementation shown, the tissue retention belt 102 includes a maximum width $W_1$, a minimum width $W_2$, and an overall length $L_1$. In the implementation shown, the maximum width is located at the primary anchor zone 110, while the minimum width $W_2$ is measured along the tension zone 112. Accordingly, the tissue retention belt 102 includes a relatively wider primary anchor zone 110 and a relatively narrower tension zone 112. In this implementation, the secondary anchor zone 114 has about the same width as the tension zone 112. However, in other implementations the secondary anchor zone 114 may have a width greater than or smaller than the width of the tension zone 112. Though the dimensions of the tissue retention belt 102 may vary, in some implementations the maximum and minimum widths $W_1$, $W_2$ are between about 1 and 20 inches, although other widths, both larger and smaller are contemplated. The longitudinal length $L_1$ may be selected based on the patient and the anticipated anchoring locations. However, in some embodiments, the longitudinal length $L_1$ may be within a range of about 24 to 72 inches, although other lengths, both larger and smaller, are contemplated. In some examples, the longitudinal length $L_1$ may be within a range of about 48 to 72 inches.

In this embodiment, the primary anchor zone 110 has a circular shape, forming a bulbous distal end of the tissue retention belt 102. The primary anchor zone 110 may be formed to have an area sufficiently large to provide satisfactory anchoring without tissue damage in most circumstances. Some examples of the first anchor zone are sized with an area to carry a load of at least 5 lbs when adhered to the patient's skin. In some examples, the primary anchor zone 110 may have an area in a range of about 20 to 200 square inches. Other dimensions, both larger and smaller, are also contemplated. In examples that are relatively circular, as is shown in FIGS. 1-3, the primary anchor zone 110 may have a radius in the range of about 2 to 8 inches, although other radiuses, both larger and smaller are contemplated. Although shown as relatively circular, primary anchor zones in other embodiments include other shapes. For example, the primary anchor zone 110 may be relatively square, rectangular, oval, kidney shaped, or may have other shapes. In some implementations, the primary anchor zone 110 is sized with a width equal to a width of the tension zone 112. Accordingly, in these embodiments, the primary anchor zone 110 may appear as a portion of a strap with a relatively constant width of parallel edges forming the tissue retention belt 102 over its overall length $L_1$.

The tension zone 112 extends from the primary anchor zone 110 to the secondary anchor zone 114, and may have a length $L_2$ within a range of about 12 to 64 inches, although larger and smaller lengths are contemplated. The tension zone 112 may have a width matching the minimum width $W_2$ or may have a width falling between the minimum width $W_2$ and the maximum width $W_1$. In some embodiments, the minimum width $W_2$ and the maximum width $W_1$ are equal. In some embodiments, the width of the tension zone 112 is in the range of about 1 to 6 inches, while in other embodiments, the width of the tension zone 112 is in the range of about 1 to 3 inches. Other widths are also contemplated.

In the implementation shown, the secondary anchor zone 114 has the same width as and is an extension of the tension zone 112. The secondary anchor zone 114 may be disposed at a proximal end of the tissue retention belt 102 or may be disposed distal of the proximal end. The location of the secondary anchor zone 114 may be defined simply by the portion of the tissue retention belt 102 that overlaps and connects with the separable anchor pad 104 in FIG. 1. In some implementations, secondary anchor zone 114 may be formed of a material attachable to the separable anchor pad 104, while in other implementations, the secondary anchor zone 114 may be formed to fold or bend and attach to itself. In some implementations, the secondary anchor zone 114 comprises an adhesive that attaches directly to the patient or an inanimate object. In such implementations, the separable anchor pad 104 may be not utilized. The secondary anchor zone 114 may have a width that matches the width of the tension zone 112. Accordingly, it may be in the range of about 1 to 6 inches in some embodiments, while in other embodiments it may be in the range of about 1 to 3 inches. In some implementations, the secondary anchor zone 114 may be sized and shaped to mimic the primary anchor zone 110. For example, in some implementations, the secondary anchor zone 114 is bulbous shaped and has a relatively circular adhesion zone. Accordingly, the widths and sizes described herein relating to the primary anchor zone 110 may also apply to the secondary anchor zone 114.

Material properties and structure of the tension zone 112 determine its yield strength or elasticity. For example, the width, thickness, and material of the body portion 140, (in combination with the other layers of the tension zone 112) may be selected to provide desired yield or elasticity characteristics. Furthermore, these may be selected to cooperate with the adhesive and size of the primary anchor zone 110 in the secondary anchor zone 114 so that, in use, the tension zone 112 stretches before the primary anchor zone 110 begins to detach from the patient's skin or before the secondary anchor zone 114 detaches or before the separable anchor pad 104 begins to detach from the patient's skin. In the following descriptions, the hook and loop fastener is designed to hold the described shear load without failure. For example only, in implementations where the primary anchor zone 110 has adhesive properties such that it begins to detach from the patient's skin at peel loads of three oz/inch width at 180 degree peel, then the tension zone 112 may be designed to elongate either elastically or in-elastically at loads less than three oz/inch width applied at 180 degrees. Accordingly, in implementations having a primary anchor zone width of 5 inches, loads of 15 oz at 180 degrees are required to peel the anchor pad at 180 degrees. This example however, is not limiting as it is contemplated that other levels of adhesion or bond strength also may be implemented. In some implementations, an additional safety factor may be included, such that the body portion 140 (or the entire tension zone 112) begins to stretch at, for example, loads less than 90% of the peel load. In other words, using the example above, the safety factor may be applied so that the body portion 140 begins to stretch at loads less than 90% of 15 oz at 180 degree peel or equivalently 13.5 oz. The safety factor may be 80%, 60%, or other factor between 0% and 100%.

In other implementations, the tension zone 112 elongates either elastically or in-elastically before the primary anchor zone 110 or the secondary anchor zone 114 begins to damage the patient's skin, thereby avoiding blistering, tearing or separation of skin layers, or other damage that may occur by inadvertent overloading. As an example, if skin damage occurs under shear loads of 40 oz/in$^2$ of skin and the primary anchor zone 110 has an area of 12 in$^2$, then the tension zone 112 may be formed so that the body portion 140 (or the entire tension zone 112) stretches at loads less than 480 oz or equivalently at loads less than 30 lb. In some implementations, an additional safety factor may be included, such that the body portion 140 (or the entire tension zone 112) begins to stretch at, for example, loads less than 90% of the anchor pad area multiplied by the skin shear force. In other words, using the example above, the safety factor may be applied so that the body portion 140 begins to stretch at loads less than 90% of 12 in$^2$ multiplied by 40 lbs/in$^2$, equaling 432 oz or equivalently 27 lb. The safety factor may be 80%, 60%, or other factor between 0% and 100%. The load value at which skin damage occurs, or at which skin integrity is compromised, may vary depending on the age of the patient, the location of the anchor pad on the body, the angle of the force applied, the amount of time the force is applied, the dwell time of the adhesive, skin properties such as porosity and moistness, and other factors. It is contemplated that the tension zone may have properties that permit it to elastically or in-elastically elongate at loads of about 60 lbs in some implementations. Elongation is considered to have occurred when the tension zone 112 stretches more than 2% of the length between anchoring points. In some implementations, the tension zone 112 elongates at loads of about 40 lbs, while in other implementations, at loads of about 30 lbs. In yet other implementations, it elongates at loads of about 20 lbs. Further implementations have properties that permit elongation at about 10 lbs. Other force amounts, smaller and greater than those identified also may be used. It should be noted that the tension zone 112 may include substantially homogenous or substantially uniform material properties along its length between the anchoring points. In other implementations, minor interruptions in uniform properties also are contemplated.

In some implementations, the tension zone 112 is designed to carry tension loads, but to not carry compression loads. Accordingly, it can be folded or rolled for packaging, and then unfolded or unrolled for use, having properties as a non-distensible or distensible fabric material.

The separable anchor pad 104 shown in FIGS. 1 and 1A includes a pad body portion 170 and an attachment surface 172. A biocompatible adhesive layer 174 is disposed on the pad body portion 170 and is configured to adhere directly to a patient's skin or an inanimate surface. In some embodiments, the adhesive of the adhesive layer 174 is configured to easily release from the patient's skin with minimal damage or soreness after a medical procedure is complete. In some embodiments, prior to use, the adhesive layer 174 faces a non-stick removable backing (not shown) that can be peeled away to reveal the adhesive layer 174 on the pad body portion 170.

The attachment surface 172 is configured to face away from the patient's skin and provides an interfacing surface to releasably fasten to the secondary anchor zone 114 of the tissue retention belt 102. The attachment surface 172 includes a releasable fastening feature that may be, for example, a part of a hook and loop fastening system or a releasably adhesive system. While hook and loop fastening systems are disclosed as being used in the illustrated implementations, it is contemplated that in further implementations alternative releasable fastening mechanisms are employed. For example, such releasable fastening systems have a greater shear strength than peel strength and may include, but without limitation to alternative structures, magnetic couplings, specialized adhesives, ratchet teeth, directional specific fibers, among others. In the exemplary implementation shown, the fastening feature comprises hooks of a relatively rigid hook portion of the hook and loop fastening system. In some implementations, the fastening feature is included over substantially the entire attachment surface 172 of the anchor pad 104 as a plurality of hooks.

In some implementations, the anchor pad 104 is at least partially flexible and conforms to contours of a patient's body shape. For example, the anchor pad 104 is sufficiently flexible to conform about a patient's curved shoulder, neck, or about edges of mechanical structures or other inanimate objects, such as a mattress, a bedframe, a support structure, or other features. It may have the rectangular shape shown, or may have other alternative shapes, such as circular, crescent, oval, triangular, or any other suitable shape. In the exemplary implementation shown, the anchor pad 104 includes rounded corners that enable the anchor pad 104 to more comfortably adhere to the patient's skin and are less likely to cause irritation. In the exemplary implementation shown, the anchor pad 104 includes a width $W_p$ and a length $L_p$ with the width $W_p$ being greater than the length $L_p$. In some implementations, the width $W_p$ is in the range of 5-14 inches long and the length $L_p$ is in the range of 4-8 inches long. In other implementations, the width $W_p$ is in the range of 7-8 inches long and the length $L_p$ is in the range of 5-6 inches long. Thus, in some aspects, the anchor pad 102 has an area ranging from 20 to 112 square inches. Other dimensions, both larger and smaller, are also contemplated.

Because in the implementation shown, the anchor pad 104 has a width $W_p$ greater than the width $W_2$ of the secondary anchor zone 114, the anchor pad 104 acts to laterally distribute loading from the secondary anchor zone 114 along an area of adipose tissue having a greater width than the overlap area. Further, because the attachment surface 172 of the anchor pad 104 includes the attachment features, which in the example shown are hooks of a hook and loop fastener, the secondary anchor zone 114 is disengaged from the anchor pad 104 and reattached with little effort in a different location on the anchor pad 104, permitting easy tension zone adjustment to an infinite number of locations on the anchor pad 104. Naturally, this same adjustment to any of a number of locations may be made on the secondary anchor zone 114. Still further, once the secondary anchor zone 114 is engaged to anchor pad 104, the attached adipose tissue will be held in a desired location.

The adhesive used to form the adhesive layer 174, the adhesive layer 122, and the adhesive layer 142 is selected to have material properties permitting it to be peeled from the patient's skin after the procedure is complete by pulling a corner or edge from the skin at an angle from the skin within a range from about 10 to 170 degrees while maintaining skin integrity, or without damaging the skin. In some implementations, the adhesive is a body worn medical adhesive from any of a variety of adhesive providers including 3M.

Referring to FIG. 1, the width $W_2$ of the secondary anchor zone 114 is shown as less than the width $W_p$ of the anchor pad 104. In some implementations, the ratio of the width $W_p$ of the anchor pad 104 to the width $W_2$ of the secondary anchor zone 114 is within a range of 1.5:1 to 4:1. In some implementations, the ratio of the width $W_p$ of the anchor pad 104 to the width $W_2$ of the secondary anchor zone 114 is within a range of 2:1 to 3.5:1. Other ratios, both larger and smaller than those identified here also are contemplated.

The anchor pad 104 and secondary anchor zone 114 together define an overlap area represented by the area of the secondary anchor zone 114 that is selectively fastened to the anchor pad 104. FIG. 1 shows this overlap area having a length Lo which is the maximum length of the secondary anchor zone 114 fastened to the anchor pad 104 and having an overlap width Wo which is the maximum width of the secondary anchor zone 114 fastened to the anchor pad 104. In FIG. 1, the overlap length Lo and the overlap width Wo are substantially the same as the respective anchor pad length $L_p$ and the tension zone width $W_2$. However, the overlap area may differ from that shown and is dependent upon where the secondary anchor zone 114 is placed on the anchor pad 104. Furthermore, it is contemplated that in alternative implementations, the width of the fiber loops is less than the width of the secondary anchor zone 114. Thus, in these implementations, the overlap area (defined as the area of the secondary anchor zone 114 that is selectively fastened to the anchor pad) is less than the area of the secondary anchor zone 114 that overlies, but does not fasten to, the anchor pad 104. In some implementations, the ratio of anchor pad area to overlap area is within a range of 1:1 to 6:1. In other implementations, the ratio is within a range of 1.5:1 to 5:1, and in yet other implementations, the ratio is within a range of 2:1 and 4:1.

In some implementations, the primary anchor zone 110 and the secondary anchor zone 114 (with or without the anchor pad 104) are selected to provide a 135 degree closure peel strength average within a range of about 1-10 oz/inch width and more particularly, within a range of about 1-8 oz/inch width, and more particularly about 2-6 oz/inch width. In other implementations, they are selected to have a 135 degree closure peel strength average within a range of about 3 oz/inch width. It is contemplated that in high tension applications of one implementation, the 135 degree closure peel strength is approximately 32 oz/inch width. In a preferred implementation, the adhesive to skin peel strength is greater than the closure peel strength. For example, in one aspect, the skin peel strength is at least twice as great as the closure peel strength. In a further implementation, the hook and loop closure peel strength is less than 50%, and preferably less than 25%, of the adhesive to LDPE, 180 Degree peel of the anchor pad adhesive. Still further, the shear strength of the hook and loop fastening system described herein is substantially greater than the closure peel strength. For example, the shear force applied to the tension zone/anchor pad overlap area described above can be as high as 80 pounds while the hook and loop closure peal strength at 135 degrees is less than 10 oz/inch width. Thus, in one aspect, the force needed to decouple the hook and loop fastening assembly is less than 20 oz. while the shear strength to hold tissue is at least as large as 80 pounds.

The longitudinal length $L_1$ of the tissue retention belt 102 is long enough to extend from a patient's abdominal region, around the patient's shoulder or neck and back to the abdominal region. In some implementations, the tissue retention belt 102 has a length long enough to extend from the patient's abdominal region to an area above the patient's head to attach to a stable structure, such as a surgical bed. The anchor pad 104 and the tissue retention belt 102 may be formed of a non-radiopaque material permitting them to be used without affecting radiology processes or treatments.

In some implementations, the secondary anchor zone 114 comprises a folding anchor portion that may be looped about a physical structure, and then reattached to itself. In such an anchor zone, one portion of the anchor zone may include, for example, a hook portion and another portion may include a loop portion. By looping the anchor portion about a mechanical structure the hook and loop portions may connect and secure the secondary anchor zone 114 about the mechanical structure.

Figure 4:
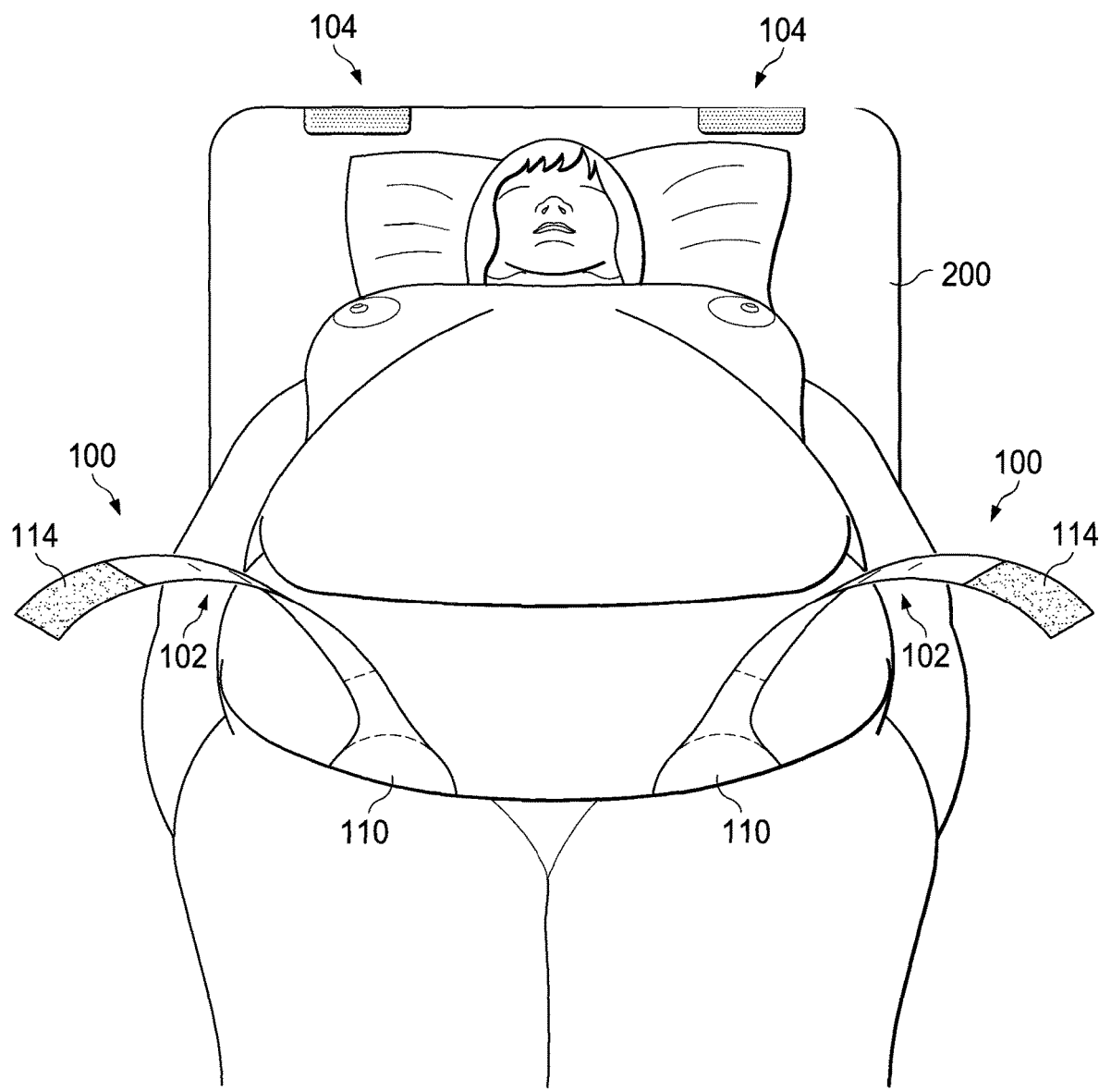
FIG. 4 is an illustration of an obese patient showing the pannus or abdominal apron with the tissue retention system according to an exemplary implementation of the present disclosure.

FIG. 4 shows an example of an obese patient laying on a hospital surgical table in a position for a surgical procedure, such as, for example, a cesarean section. The procedure includes placing the patient on the operating room table per protocol, generally in supine position with a left lateral tilt. As shown, the patient has a pannus or abdominal apron entirely covering the lower abdomen. In order to perform the procedure, the operating physician is required to expose the lower abdomen by displacing the pannus. The physician or other health care provider may lift the pannus and then scrub the abdomen per hospital policy with a cleanser such as alcohol or Betadine scrub. It is contemplated, however, that in some instances, a part of or the entire pannus displacement procedure, as described below, may occur prior to scrubbing or prepping the pannus. The adhesive described above maintains its adhesion in the presence of cleansers such as alcohol and Betadine scrub.

The removable backing 121 may be removed from the primary anchor zone 110 to expose the adhesive layer 122 (FIG. 3). The primary anchor zone 110 may then be applied directly to the skin on the lower abdomen so that the adhesive layer 122 on the primary anchor zone 110 securely adheres to the skin. If using a non-incisable primary anchor zone 110, care should be taken to not place the primary anchor zone 110 over skin intended for incision. In addition, care should be taken to arrange the primary anchor zone 110 so that the tension zone 112 and the secondary anchor zone 114 extend in the direction to be pulled in tension. That is, the tension axis 134 of the tension zone 112 should be aligned in a direction of desired tension.

FIG. 4 shows two tissue retention systems 100 with primary anchor zones 110 applied to the underside of the pannus so that an upper portion of the primary anchor zone 110 protrudes outwardly from the folds of skin. The anchor pad 104 may, in some implementations, be applied to a desired anchoring location. This may include removing backing material to expose the adhesive layer 174, and then adhering the anchor pads 104 to the desired location about the surgical room. In this exemplary implementation, the separable anchor pads 104 are disposed at an end of the surgical bed 200. In other implementations, the separable anchor pads 104 may be placed at additional locations on or about the patient. In some implementations, the separable anchor pads 104 may be disposed on the patient's shoulders. These anchor pads 104 also serve to connect to the secondary anchor zone 114 of the tissue retention belt 102 as described below.

With the primary anchor zones 110 applied to the skin of the pannus, the healthcare provider may grasp the tension zone 112 or the secondary anchor zone 114 and pull in the direction of desired pannus movement. Accordingly, the tension zone 112 may extend along the tension axis in a direction of loading to be applied to retained tissue. The tension axis aligns with and is representative of the direction that a health care provider desires the tissue to move. The healthcare provider may continue to apply tension to the tissue retention belt 102 in the direction of desired tissue movement and by using the tissue retention belt 102 the healthcare provider may lift or displace the pannus to a desired position.

A healthcare provider may use the auxiliary anchor zone 130 on the tension zone 112 to provide additional adhesive support and to further distribute loading over a larger contact area of the patient's skin. The auxiliary anchor zone 130 enables a healthcare provider to customize the technique by using a larger adhesive contact area depending upon the need and preference of the healthcare provider. Because healthcare providers can choose whether or not to use the auxiliary anchor zone 130, there is no need to apply adhesive layers onto the skin of the patient when it is not necessary or desired. Because of this, removal of the adhesive layers from the skin can be expedited, making cleanup after a surgical procedure more efficient, thereby reducing the overall time of the surgical procedure. In addition, if any adjustment is desired, there may be a smaller adhesive area to be peeled free prior to making the adjustment. However, if the auxiliary anchor zone 130 is needed or desired, healthcare providers can also adhere the auxiliary anchor zone 130 to the patient's skin. This may be done to further distribute loading over a larger skin area to protect the patient, or may be done during the surgical procedure if perspiration or moisture on the skin begins to impact adhesion of the primary anchor zone 110 during the surgical procedure.

If the healthcare provider decides to apply the auxiliary anchor zone 130, he or she may first remove the removable backing 144 and then apply the auxiliary anchor zone 130 directly to the skin so that the adhesive layer 142 securely adheres to the skin. Then by grasping and pulling the tension zone 112 and/or the secondary anchor zone 114, the healthcare provider may displace the pannus or other skin in the desired direction of tension.

When the displaced tissue is in a desired position, the secondary anchor zone 114 may be fixed in place to maintain the displaced tissue in the desired position. In some implementations, the secondary anchor zone 114 may attach to the separable anchor pads 104. In other implementations, the secondary anchor zone 114 may include its own adhesive layer, and may attach directly to the patient or to other equipment within the surgical room. For example, the secondary anchor zone 114 may attach to a mechanical structure or other inanimate object such as the bed frame or mattress, the shoulder of the patient, or other locations as described herein or about the surgical room.

Figure 5:
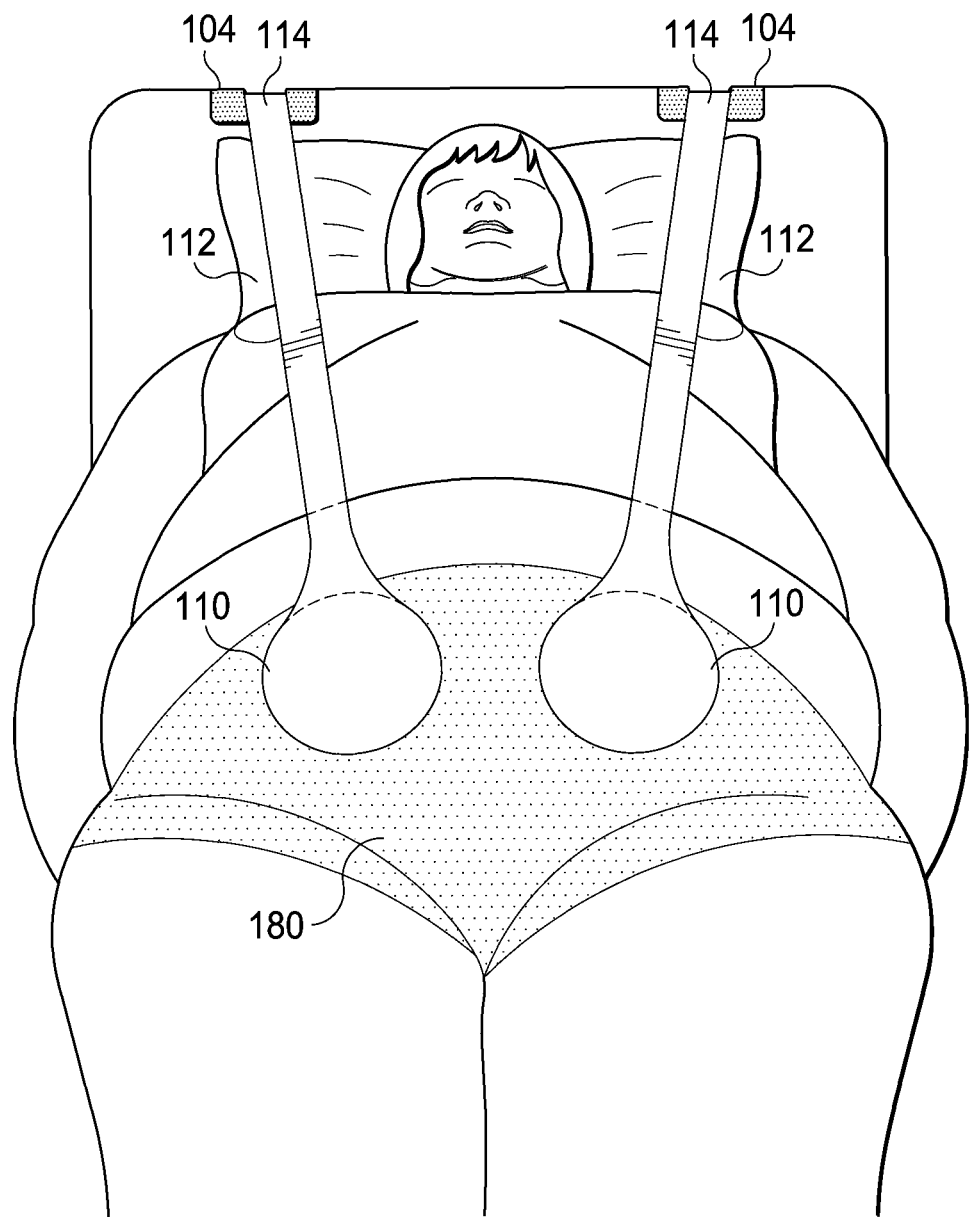
FIG. 5 is an illustration of the obese patient with the pannus or abdominal apron maintained in a displaced position using the tissue retention system according to an exemplary implementation.

FIG. 5 shows the tissue retention system 100 in an assembled position, with the tissue retention belt 102 anchored to the separable anchor pad 104. In the implementation shown, the primary anchor zone 110 at the distal end of the tissue retention belt 102 is adhesively adhered to the pannus while the proximal end of the tissue retention belt 102 is tensioned and attached to the separable anchor pad 104 disposed at the end of the bed. Here, as discussed above, the anchor pad 104 includes a hook material and the secondary anchor zone 114 includes a loop material. Although shown in a particular location on the pannus, it is contemplated that the primary anchor zone 110 may be placed in any desired regions, including the supra pubic region of the body. The shaded area 180 represents an area that is normally hidden where the skin of the pannus rests against the skin of the lower abdomen.

In some implementations, the tissue retention belt 102 does not attach to anchor pads disposed on the patient's shoulders or other body portion, but may extend behind the patient's neck or about the patient's shoulder and the secondary anchor zone 114 returns and attaches to the pannus. Thus, a single tissue retention belt 102 may be used to secure the pannus.

During or while still preparing to perform the medical procedure, the location of the tissue retention belt 102 may be adjusted at the secondary anchor zone 114. This is accomplished by simply detaching the secondary anchor zone 114 from the anchor pad 104, moving the pannus and/or the secondary anchor zone 114 to the desired position, and reattaching the secondary anchor zone 114 to the anchor pad 104. In some implementations, detaching the secondary anchor zone 114 from the anchor pad 104 is simply accomplished by pulling the secondary anchor zone 114 to detach the attachment features, such as the hook and loop portions. The secondary anchor zone 114 is then re-attached at the desired location. In this way, the pannus can be adjusted simply by manipulating the secondary anchor zone 114. Because the tissue retention belt 102 includes a non-adhering contact region 132, adjustment or revision of the connection location of the tissue retention belt 102 may be relatively easily accomplished. For example, if the tension zone 112 were adhered to the patient along its entire length, adjustment of the secondary anchor zone 114 would also require separation of the adhesive layer 142 of the tension zone 112 from the patient before an adjustment could be made.

Figure 6:
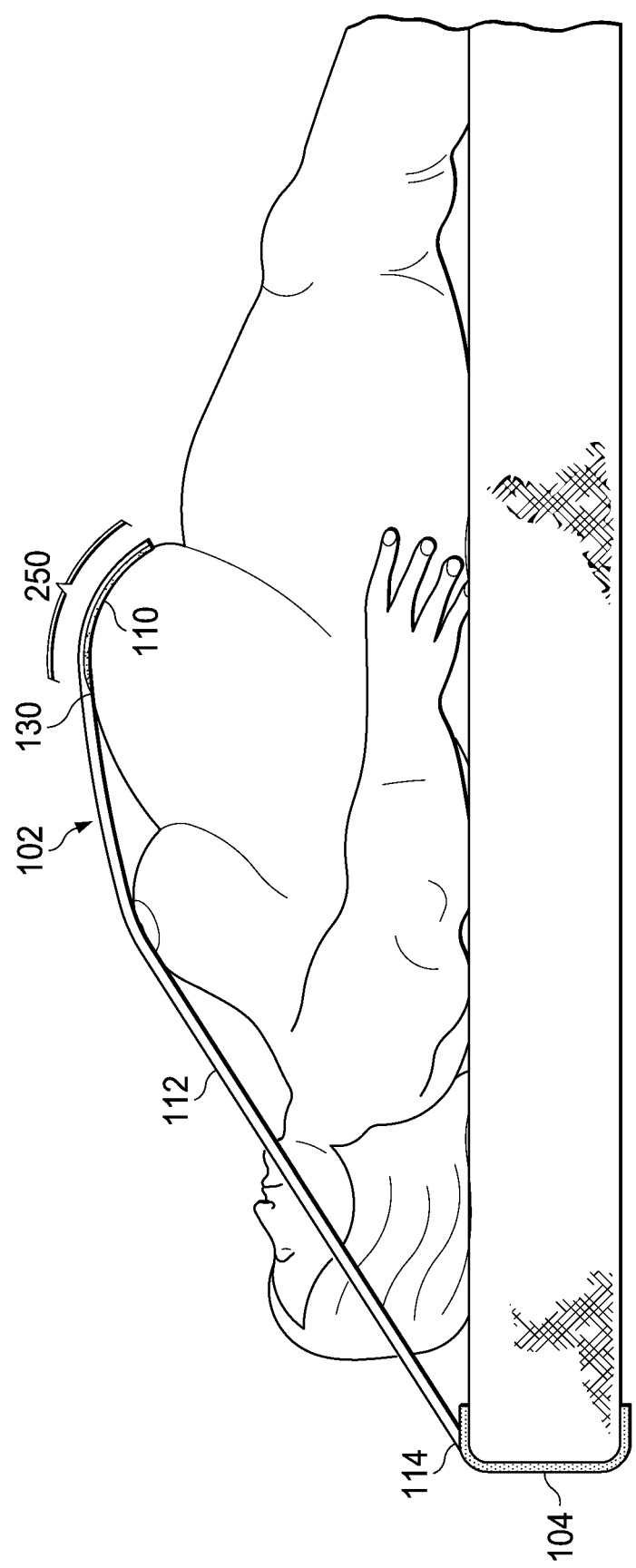
FIG. 6 is an illustration of a side view of an obese patient with the pannus or abdominal apron maintained in a displaced position using a main anchor zone.
Figure 7:
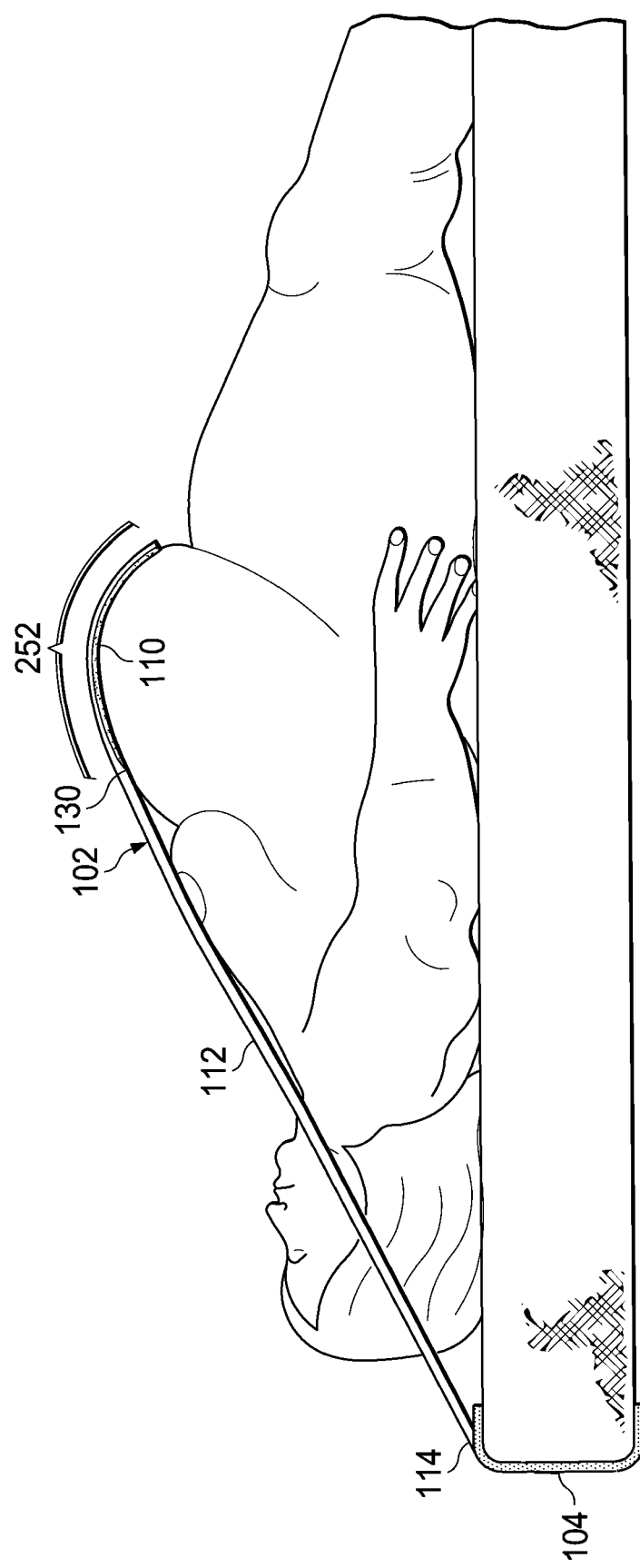
FIG. 7 is an illustration of a side view of an obese patient with the pannus or abdominal apron maintained in a displaced position using both the main anchor zone and the auxiliary anchor zone.

FIGS. 6 and 7 show a side view of the patient with a pannus displaced to expose regions of skin for surgical access. FIG. 6 shows an adhesive area 250 including only the primary anchor zone 110. In this embodiment, the auxiliary anchor zone 130 is still covered with the removable backing 144 and therefore not in contact with the skin. In contrast, FIG. 7 shows an adhesive area 252 including both the primary anchor zone 110 and the auxiliary anchor zone 130. As can be seen, since the auxiliary anchor zone 130 forms a portion of the tension zone 112, using the auxiliary anchor zone 130 increases the size of the adhesion area in the direction of the tension axis.

Once the adipose tissue is securely displaced to expose the surgical site, the healthcare provider may perform the medical procedure. For example, in one exemplary procedure, such as a cesarean section, the initial steps of pre-positioning the adipose tissue includes exposing the surgical site where the surgical procedure will be performed as explained above. The incision site is then prepared. An incision, such as a transverse incision, a midline incision, or other suitable incision, may be made in the lower abdomen. In one aspect, after making the incision, one or more retractors may be used to further enlarge the size of the opening and/or to retract fat, muscle, blood vessels, and other structures below the surface of the skin. The procedure continues with the baby being born through the opening. Any retractors used during the procedure are removed from the incision. In some applications, such as child birthing, the change in the patient's abdominal size will naturally reduce the force on the tissue retention belt. However, if increased tension and/or a further reduction in tension is required, the force on primary anchor zone 110 may be modified by momentarily disengaging the secondary anchor zone 114 and then reattaching it in an alternative tensioning position while further medical steps of the procedure are completed on the patient. For example, the placenta may be delivered through the incised opening while the tension zones are in the alternative tensioning position. Eventually, the opening is sutured closed. In a preferred method, once the surgical procedure is complete, the secondary anchor zone 114 may be released from its anchoring point and the auxiliary anchor zone 130 and primary anchor zone 110 may be carefully peeled from the patient's skin.

Figure 8:
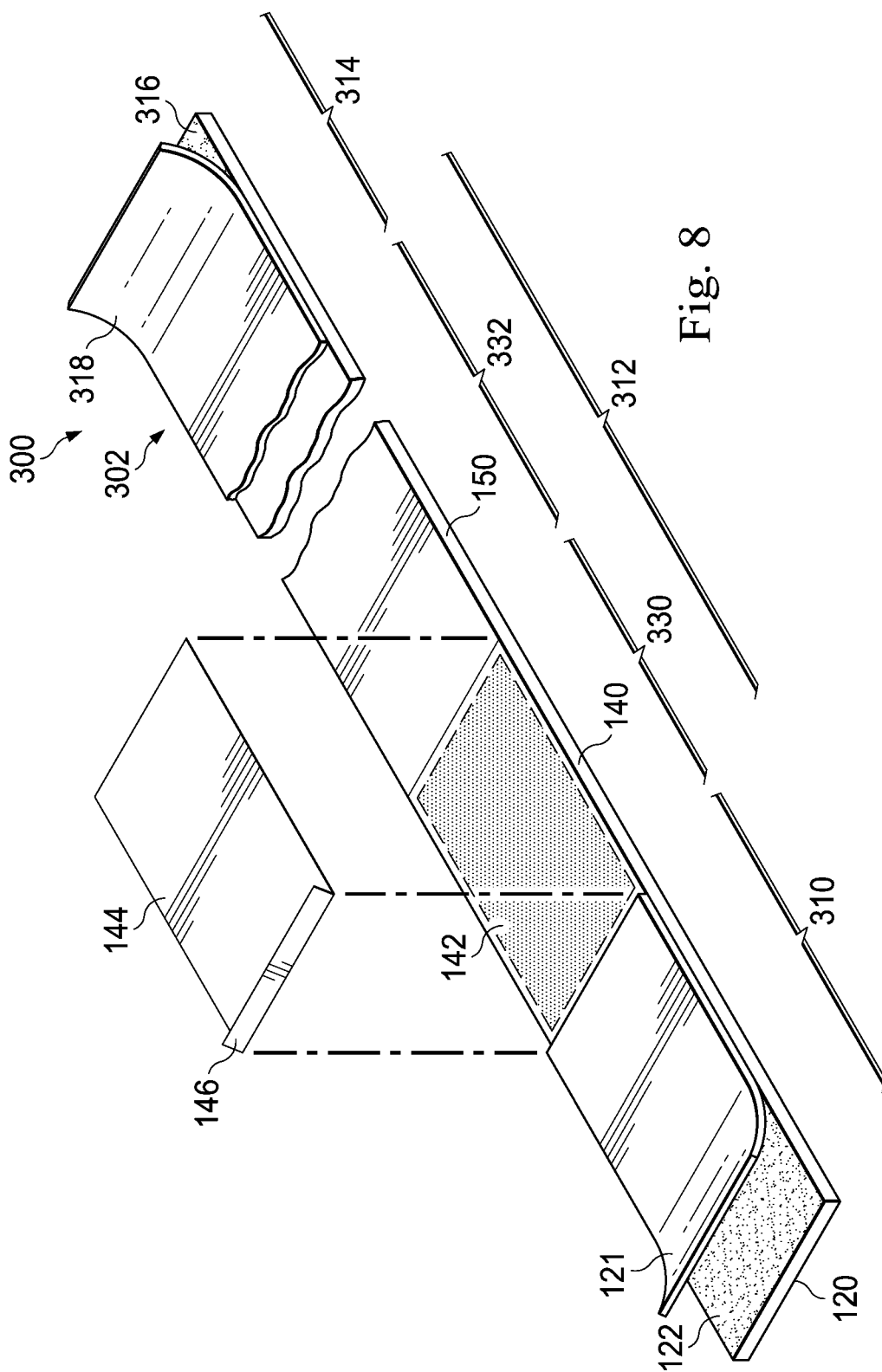
FIG. 8 is an illustration of a perspective view of another exemplary tissue retention belt having an auxiliary anchor zone according to an exemplary implementation of the present disclosure.

FIG. 8 shows an alternative tissue retention system 300. Here, the tissue retention system 300 includes a tissue retention belt 302 with a primary anchor zone 310, a tension zone 312, and a secondary anchor zone 314. The primary anchor zone 310 includes many features already described with reference to the primary anchor zone 110. As such, the description relating to the primary anchor zone 110 is also applicable to the primary anchor zone 310. For example, the primary anchor zone 110 includes the body portion 120 and the adhesive layer 122. FIG. 8 also shows the removable backing 121 on the primary anchor zone 310. In this implementation, however, the primary anchor zone 310 is shaped differently than the primary anchor zone 110. Here, the primary anchor zone 310 is formed at the distal end of the tissue retention belt 306 with a width that is generally the same as the width of the tension zone 312. As described above, the width of the primary anchor zone 310 in this implementation may be within the range of about 3 to 12 inches, although widths both larger and smaller are contemplated. In some implementations, the width is within a range of about 3 to 6 inches. Other ranges are contemplated. The longitudinal length of the primary anchor zone 310 may be selected to take into account the width of the primary anchor zone 310 to provide a primary anchor area within a range of about 20 to 112 in$^2$, although larger and smaller areas are contemplated. In some implementations, the longitudinal length of the primary anchor zone 310 is in the range of about 4 to 10 inches, although larger and smaller longitudinal lengths are contemplated.

The tension zone 312 also includes an auxiliary anchor zone 330. The auxiliary anchor zone 330 may include features similar to the auxiliary anchor zone 130, and the description relating to the auxiliary anchor zone 130 may also apply to the auxiliary anchor zone 330. For example, although a slightly different shape, the auxiliary anchor zone 330 includes the adhesive layer 142, the removable backing 144, and the graspable tab 146. The tension zone 312 also includes the non-adhering contact region 332 and the body portion 150 of the non-adhering contact region 332.

The secondary anchor zone 314 includes many features already described with reference to the secondary anchor zone 114. As such, much of the description relating to the secondary anchor zone 114 is also applicable to the secondary anchor zone 314. In this embodiment, however, the secondary anchor zone 314 includes an adhesive layer 316 and a removable backing 318. Therefore, this embodiment of the tissue retention belt 302 may function without a separable anchor pad. Instead, the secondary anchor zone 314 may be adhered directly to the patient or an inanimate object such as the surgical bed, or may be adhered to some other anchoring structure in the surgical room. In implementations where the secondary anchor zone 314 includes an adhesive layer, the adhesive may be the same as that described above with reference to the primary anchor zone 110.

Figure 9:
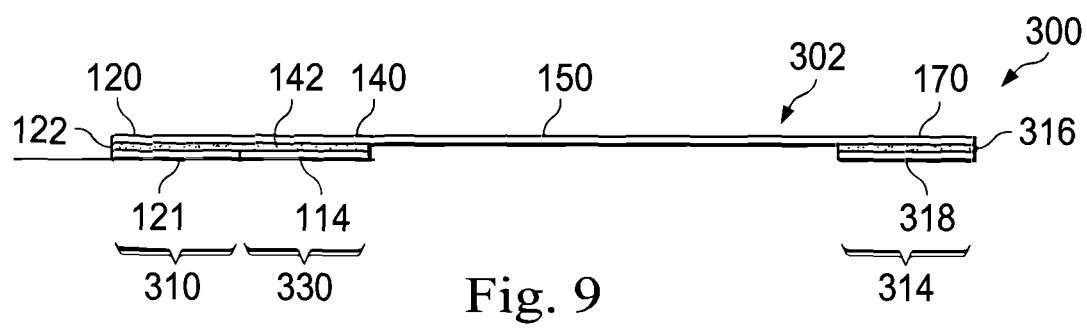
FIG. 9 is an illustration of a side view of another exemplary tissue retention belt having an auxiliary anchor zone according to an exemplary implementation of the present disclosure.

FIG. 9 shows one example of a side view of the tissue retention system 300 of FIG. 8. As noted, the removable backing 121 of the primary anchor zone 310 may be removed to allow tissue retention belt 302 to secure to the skin of the patient. Likewise, the removable backing 144 of the auxiliary anchor zone 330 may be removed if desired. The removable backing 318 of the secondary anchor zone 314 may be removed to secure the proximal end of the tissue retention belt 302 to the patient or an inanimate object.

Figure 10:
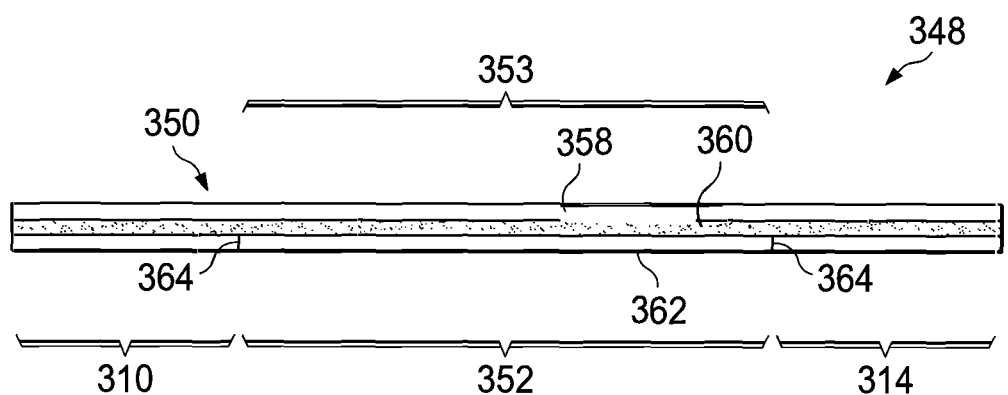
FIG. 10 is an illustration of a side view of another exemplary tissue retention belt having an auxiliary anchor zone according to an exemplary implementation of the present disclosure.

FIG. 10 shows an additional implementation of a tissue retention belt 350 of a tissue retention system 348. The tissue retention belt 350 is similar in many respects to other tissue retention belts described herein, and for simplification, the descriptions of similar features will not be re-described. In this implementation, however the tension zone 353 includes an auxiliary anchor zone 352 that extends the length of the tension zone 353. In this implementation, the auxiliary anchor zone 352 includes the body portion 358, an adhesive layer 360, and a removable backing 362. In this implementation, the adhesive layer 360 of the auxiliary anchor zone has a lower bond strength than the adhesive at the primary anchor zone 310 and the secondary anchor zone 314. The removable backing 362 may include perforations or cuts 364 that distinguish one anchor zone from another, making each backing independently removable.

Figure 11:
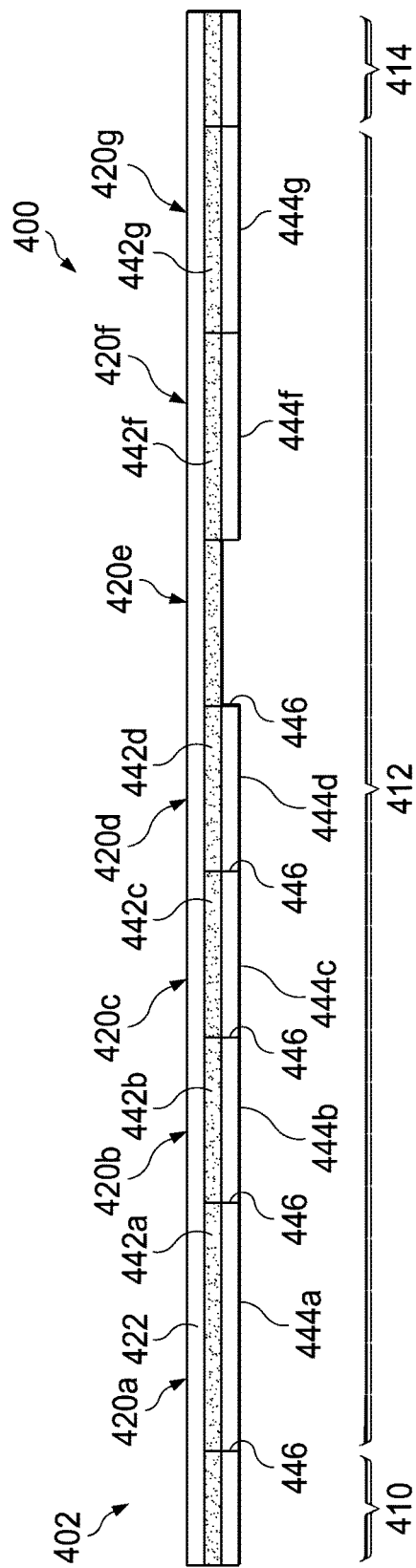
FIG. 11 is an illustration of a side view of another exemplary tissue retention belt having an auxiliary anchor zone according to an exemplary implementation of the present disclosure.

FIG. 11 introduces another tissue retention system referred to herein by the numeral 400 and comprised of a tissue retention belt 402. The tissue retention belt 402 in this embodiment includes a primary anchor zone 410, a tension zone 412, and a secondary anchor zone 414. The primary anchor zone 410 and the secondary anchor zone 414 may have features similar to those previously described, and they will not be re-described here. In this implementation, the tension zone 412 comprises a plurality of auxiliary anchor zones referenced herein by the numerals 420a, 420b, 420c, 420d, 420e, 420f, and 420g. This implementation shows seven auxiliary anchor zones together extending the entire distance from the primary anchor zone 410 to the secondary anchor zone 414. Other implementations have fewer than seven auxiliary anchor zones, or more than seven auxiliary anchor zones. Some implementations have two, three, or four auxiliary anchor zones. In some implementations, the auxiliary anchor zones extend the entire distance between the primary anchor zone 410 in the secondary anchor zone 414 as shown in FIG. 11, while in other implementations, the auxiliary anchor zones extend only a part of the distance between the primary anchor zone 410 and the secondary anchor zone 414. In some implementations, auxiliary anchor zones are disposed adjacent the primary anchor zone 410, and any non-adhering contact region that may be included in the tension zone may be disposed adjacent the secondary anchor zone 414.

In the example shown, the tissue retention belt 402 includes a continuous integrated body portion 422, and includes distinct adhesive layers and backing materials. Here, the adhesive layers and backing materials are sliced with cuts 446 so as to be distinct from one another and independently removeable. In some implementations, the cuts 446 are perforations that promote independent removal of the removable backing from one anchor zone and separating the removable backing from adjacent anchor zones. In such embodiments, the removable backing may be frangible in order to be easily torn or separated from adjacent removable backing.

Other implementations include a continuous integrated body portion 422, and a continuous integrated adhesive layer formed of the adhesive layers 442a-442g. In such implementations, the removable backing may be frangible by being precut, or may include perforations or other features that enable user to distinguish between the primary anchor zone 410 and any of the plurality of auxiliary anchor zones 420, and the secondary anchor zone 414, and remove the backing 444a-444g one anchor zone at a time without removing the backing of adjacent anchor zones as desired.

In use, a medical professional may expose the adhesive layers of the primary anchor zone 410 and the secondary anchor zone 414, and may choose to expose one or more auxiliary anchor zones 420 depending upon factors considered by healthcare providers. In some implementations, the factors may include the size of the patient, the weight of the patient, how many tissue retention belts are in use, the application, the surgical technique to be used, preference of the operating healthcare provider, and other factors.

Figure 12:
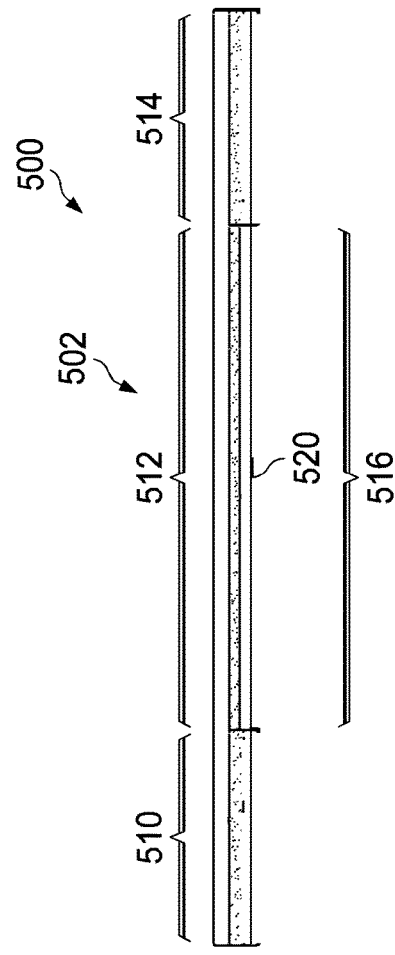
FIG. 12 is an illustration of a side view of another exemplary tissue retention belt having an auxiliary anchor zone according to an exemplary implementation of the present disclosure.

FIG. 12 illustrates another implementation of a tissue retention system 500 comprised of a tissue retention belt 502. The tissue retention belt 502 includes a primary anchor zone 510 a tension zone 512 and a secondary anchor zone 514. The primary anchor zone 510 and the secondary anchor zone 514 may have features similar to those previously described, and therefore they will not be re-described here. In this implementation, the tension zone 512 may include an auxiliary anchor zone 516 that may extend the distance between the primary anchor zone 510 and the secondary anchor zone 514. The auxiliary anchor zone 516 may be formed with the same integrated body portion as the primary anchor zone 510 and the secondary anchor zone 514. In other implementations, body portions may be permanently affixed to each other via sewing, ultrasonic welding, adhesion, or using other methods. In this implementation, the auxiliary anchor zone 516 may include different bond strength or tension characteristics. These may be due to a number of factors including, a different adhesive, a different amount of adhesive, an integrated or mixed area of adhesion, or other factors. As such, the bond strength of the primary anchor zone 510 and the secondary anchor zone 514 may be different than the bond strength of the auxiliary anchor zone. The tension zone 512 includes a removable backing 520 that covers the auxiliary anchor zone 516 and allows a healthcare provider to decide when to use the auxiliary anchor zone.

Figure 13:
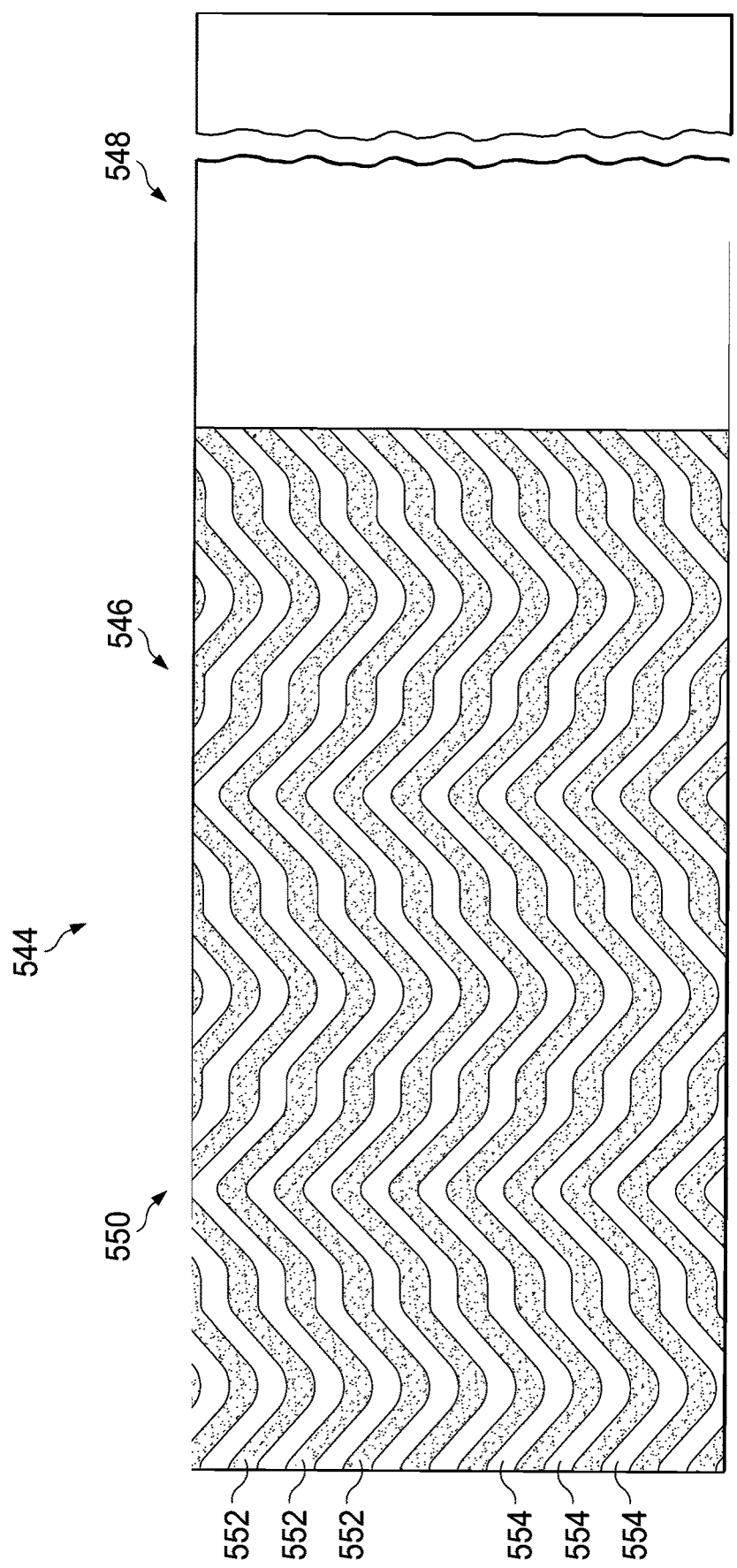
FIG. 13 is an illustration of an adhesive pattern of an anchor zone according to an exemplary implementation of the present disclosure

FIG. 13 shows one example of an adhesive pattern 550 that may form a part of any of the auxiliary anchor zones described herein. In this implementation, FIG. 13 shows an end of a tissue retention belt 544 with an anchor zone 546 adjacent a non-adhesive tension zone 548. The anchor zone 546, which represents any anchor zone in any implementation herein, includes alternatingly disposed rows of an adhesive area 552 and a non-adhesive area 554. In some implementations, the auxiliary anchor zones include such alternating adhesive pattern, while the primary anchor zone and the secondary anchor zone are completely covered by a continuous adhesive. This would create a difference in the bond strength of the auxiliary anchor zone and the primary and secondary anchor zones. In other implementations, all of the anchor zones, including the primary, the secondary, and the auxiliary anchor zones have continuous adhesive layers across their surfaces. In other implementations, the primary and secondary anchor zones also include adhesive in an alternating pattern. In some implementations, the primary anchor zone and the secondary anchor zone have the same bond strength, while in other implementations, their bond strength differs. In some implementations, the primary anchor zone has a greater bond strength than the secondary anchor zone, and the secondary anchor zone has a greater bond strength than the auxiliary anchor zone. In other implementations, the secondary anchor zone has a lower bond strength than the auxiliary anchor zone and the primary anchor zone. In some implementations, instead of having rows of an adhesive 552 and a non-adhesive area 554, the tissue retention belt includes rows of an adhesive with a first bond strength and an adhesive with a second bond strength. In yet other embodiments, the pattern includes adhesives with a height difference between rows. For example, the adhesive area 552 may have an elevation different than the non-adhesive area 554. Although shown with rows, other embodiments include adhesive droplets or shaped patches of adhesive and non-adhesive areas. In some implementations, the anchor zone includes an adhesive gradient with a greater bond strength at one portion of the anchor zone and lower bond strength at the opposing portion of the anchor zone. This may include using a larger overall adhesive area that may taper toward an area with a smaller adhesive area. For example, the rows in FIG. 13 may be wider at one end and smaller at the other to provide a gradient in bond strength.

Figure 14:
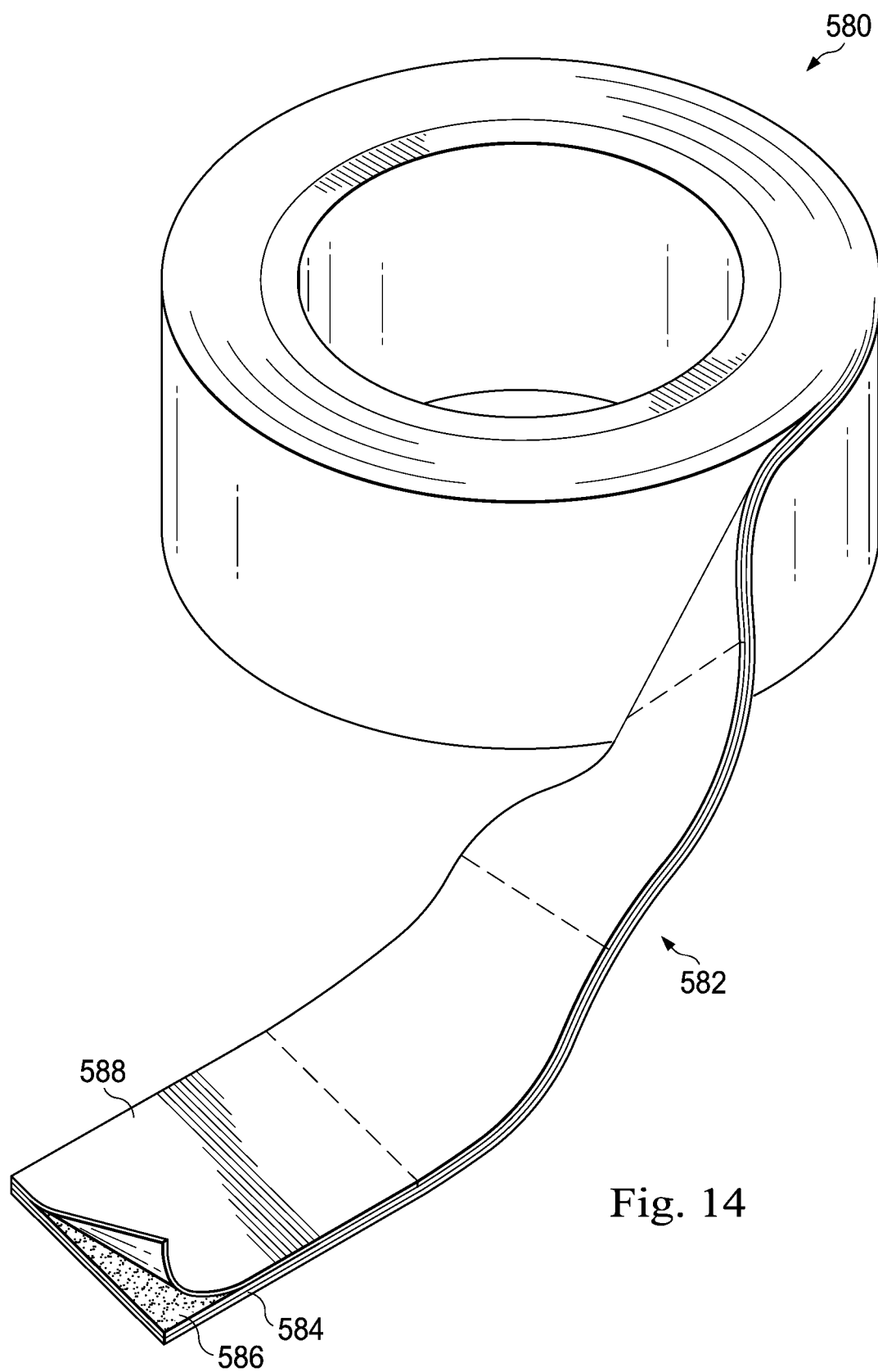
FIG. 14 is an illustration of a tissue retention belt roll according to an exemplary implementation of the present disclosure

FIG. 14 shows an exemplary implementation of a tissue retention system 580 comprised of a tissue retention belt 582 in the form of a belt roll. The belt roll may contain sufficient material to form a plurality of tissue retention belts. In some examples, the belt roll may have a total linear length in the range of 12 feet to 50 feet, although both larger and smaller ranges are contemplated. The belt roll may be formed of material as described herein and include the body portion 584, the adhesive layer 586, and the removable backing 588. In the embodiment shown, at least the body portion 584 is integrated. Depending on the implementation, the adhesive layer 286 may also be integrated. The removable backing 588 may include perforations or cuts that distinguish one anchor zone from another, making each independently removable. The removable backing may form the skin-contacting, non-adhesive surface of the tissue retention belt when the auxiliary anchor zones are not adhered to the patient. In some implementations, each of the removable backings 588 includes a tabbed portion that can easily be grasped for simple removal from the adhesive. In some implementations, the unrolled belt roll may form a tissue retention belt as shown in FIG. 11.

In use, a health care provider may unroll a tissue retention belt 582 of a desired length, thereby forming the tissue retention belt. He or she may then cut or tear a desired length from the roll. The distal portion of the tissue retention belt may be referred to as a primary anchor zone, and a proximal portion of the tissue retention belt 582 may be referred to as a secondary anchor zone. The plurality of auxiliary anchor zones between the primary and secondary anchor zones may form the tension zone. Until the removable backing is removed, the auxiliary anchor zones will not attach to a patient's skin. However, if desired based on the factors described herein, a health care provider determines to use an auxiliary anchor zone, then he or she may remove the removable backing to expose the adhesive layer of the auxiliary anchor zone.

In some surgical implementations, the belt roll may be disposed in a surgery room allowing healthcare providers to unroll and cut or tear a desired length from the belt roll. In other implementations, the belt roll may include a plurality of distinct and precut tissue retention belts. Accordingly, a user may unroll the belt roll to obtain a precut length, while remaining tissue retention belts may be maintained in roll form for storage.

Although described with reference to exposing the lower abdomen, it should be apparent that a similar method may be used to expose the groin region when access is required. This may be useful with some patients for hysterectomies and normal vaginal births of obese patients, for example. Still further, the tissue retention system may be used for long term treatments to expose tissue to speed healing and/or prevent infection. In other implementations, the first anchor zone may be attached to the underside of the patient's breast to support the adipose tissue and maintain it in a desired position. This is useful for example, in applications requiring surgical access or radiological tests. In some examples, the tissue retention system may be used for oncology purposes, including radiation treatment. In some implementations, the tissue retention system may be used on a patient's thigh in order to move the adipose tissue to provide access for a medical procedure. This may provide better visualization during repair or surgery of the groin, perineum, vaginal vault, or other areas needing better visualization under the adipose tissue. Also, the tissue retention system 100 also can facilitate access to the femoral region for all types of cardiovascular procedures, ranging from angioplasty to using a Foley catheterization and to any type of thoracic surgery that requires catheterization of the femoral artery. In other implementations, the primary anchor zone may be attached to a patient's right buttocks and a second anchor pad 104 is attached to the patient's left buttocks to displace the buttocks and expose the rectum. This may provide better visualization during, for example, hemorrhoid surgery or repair of the anus, among other procedures.

In yet other implementations, the patient is placed in a supine position with the patient's torso elevated higher than the patient's head. In so doing however, the weight of the pannus, which on some obese patients may be more than one hundred pounds, may shift to at least partially lie on the patient's lungs, rendering breathing difficult or impossible. The tissue retention system disclosed herein however, may be used to alleviate some of the weight on the lungs by maintaining the adipose tissue, such as the pannus, in its more natural location.

While the examples set forth herein primarily describe attaching the anchor pads directly to the skin, in some alternatives, the anchor pads attach to surgical drapes over an incision. Accordingly, in these instances, the anchor pads may not attach directly to the skin, but attach to the surgical drapes adhered to the skin.

Figure 15:
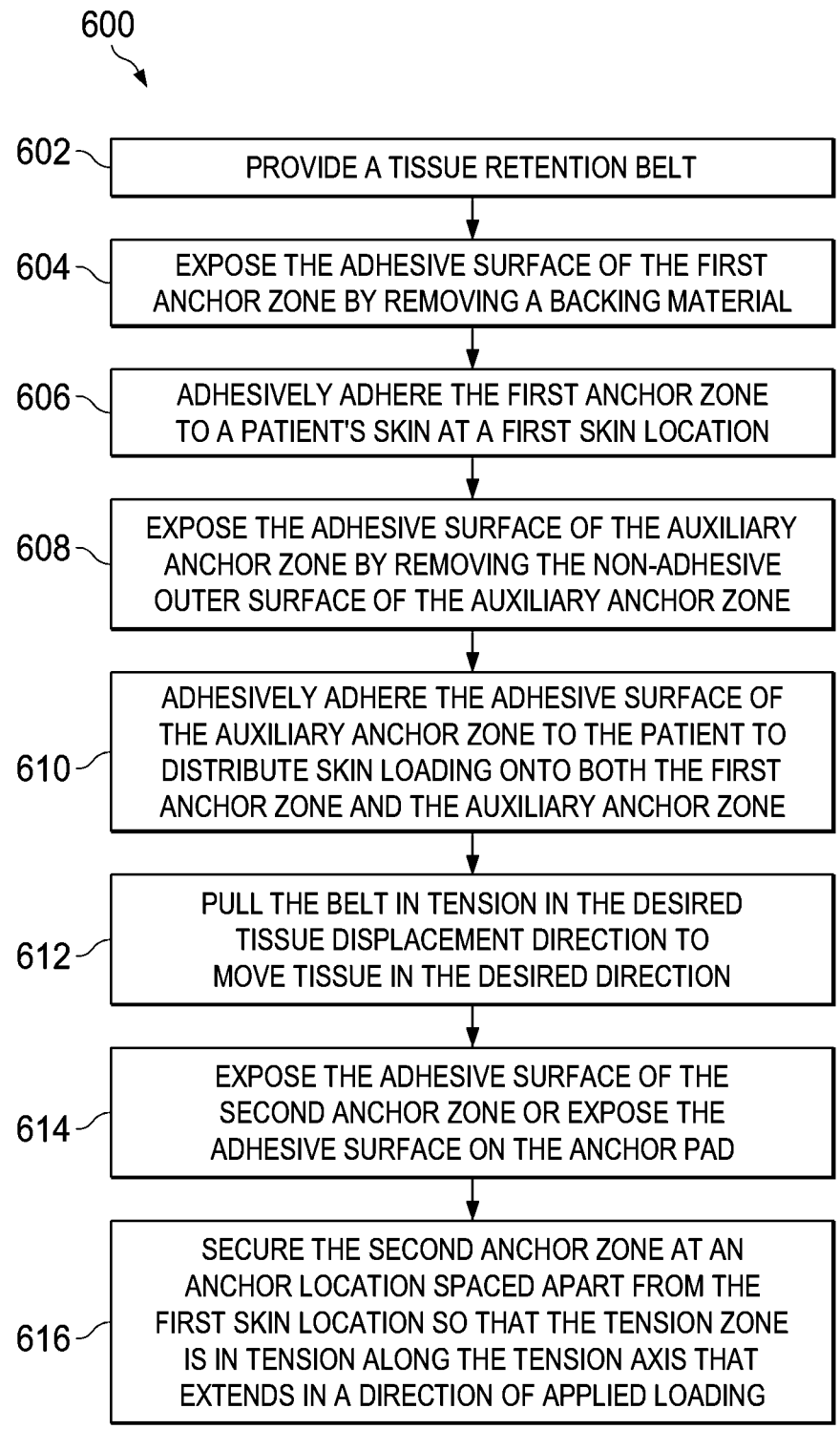
FIG. 15 is a flow chart illustrating a method of using a tissue retention system according to an exemplary implementation of the present disclosure.
Figure 16:
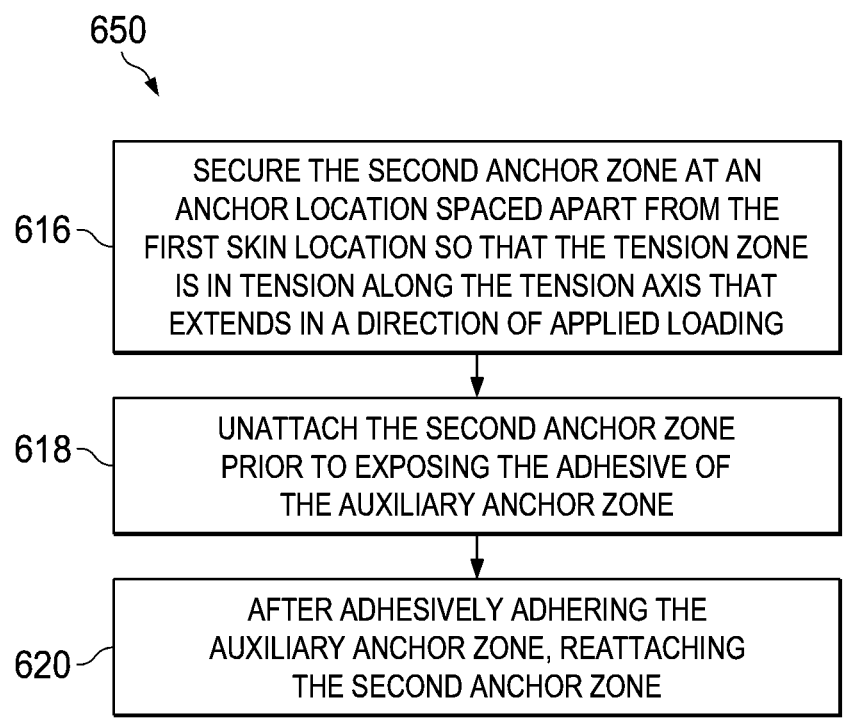
FIG. 16 is a flow chart illustrating a method of using a tissue retention system according to an exemplary implementation of the present disclosure.

FIGS. 15 and 16 are flowcharts illustrating an exemplary method 600 of retaining patient tissue in a desired position. The method may begin by preparing the patient for the medical procedure. This may include placing the patient on the operating room table per protocol. At block 602 the health care provider provides a tissue retention belt. In some implementations, this may include removing the tissue retention belt from packaging. In other implementations, this may include removing a desired length of a tissue retention belt from a tissue retention roll. Removing the tissue retention belt from a tissue retention roll may include tearing or cutting a desired length from the tissue retention roll. The tissue retention belt may be any of the tissue retention belts described herein.

At block 604, the health care provider may expose the adhesive surface of the primary anchor zone by removing the backing material. At block 606, the health care provider may adhesively adhere the primary anchor zone to the patient's skin. This may include applying the exposed adhesive surface directly to the skin on the lower abdomen to securely adhere the primary anchor zone to the skin. Care should be taken to align the tension zone in the desired direction of tissue movement so that the tension axis extends in a direction acceptable to the health care provider and when the tissue is displaced, provides the desired access for the surgical procedure.

At block 608, the health care provider may expose the adhesive surface of the auxiliary anchor zone by removing the non-adhesive backing of the auxiliary anchor zone. This may include making a determination about whether to employ the auxiliary anchor zone of the tissue retention belt. The determination may be based on any number of factors including for example, health care provider preference, the weight of the patient, the length of the procedure, the type of the procedure, and other factors described herein.

With the auxiliary anchor zone adhesive surface exposed, at block 610, the health care provider may adhesively adhere the auxiliary anchor zone to the patient. This may distribute skin loading onto both the primary anchor zone and the auxiliary anchor zone.

At block 612, the health care provider may pull the tissue retention belt in tension in the direction of the tension axis. This may displace tissue in the desired direction to provide greater access to a body region of the patient needing treatment. Since the health care provider may initially anchor one end of the tissue retention belt, in some implementations, only a single health care provider is needed to pull on the tension zone or the secondary anchor zone to displace the tissue to the desired location.

At block 614, the health care provider may expose the adhesive surface on the secondary anchor zone or expose the adhesive surface on the anchor pad. In some implementations, this may include removing the separable backing from the secondary anchor zone. In implementations employing the separable anchor pad, this may include removing the backing from the anchor pad to expose the adhesive surface of the anchor pad. In such implementations, the anchor pad is then secured at an anchoring location. This may be anywhere about the surgical site and may include locations on the patient or off the patient. In some implementations, the anchor pad may be secured to the patient's shoulder. In other implementations, the anchor pad may be secured to a mechanical structure forming an in animate object adjacent the patient. This may include portions of the surgical room bed or other mechanical structures about the patient.

At block 616, the health care provider secures the secondary anchor zone at an anchor location spaced apart from the primary anchor location so that the tension zone is tautly connected in tension along the tension axis. This may include securing the adhesive surface of the secondary anchor zone to an anchoring location. The location may be any of those described herein including the patient or inanimate objects or mechanical structures disposed about the patient. Block 616 may also include securing the secondary anchor zone to the previously placed anchor pad. In implementations using hook and loop fastening mechanisms, this may simply require moving the secondary anchor zone over the anchor pad so that they touch and connect.

With the tissue retention belt properly securing the adipose tissue in a desired position, the surgeon may then perform the procedure. When the procedure is complete, the health care provider may remove the tissue retention belt by un-attaching the secondary anchor zone from either the anchor pad, the patient, or the mechanical structure to which it is attached. It may also include carefully peeling the auxiliary anchor zone and the primary anchor zone from the patient's skin.

In some implementations, securing the anchor zone at an anchor location spaced apart from the first anchor location includes looping the second anchor zone around a physical structure, such as a bed frame, and then attaching the anchor zone to itself. For example, this may include looping a hook portion about a mechanical structure and then connecting it to a loop portion.

FIG. 16 is a flowchart showing a method 650 of revising a patient tissue retention system. The method may begin after the tissue retention system has been properly implemented according to the method shown in FIG. 15. FIG. 16 is a method that may be followed when the healthcare provider made a determination to not adhere the auxiliary anchor zone to the patient. In FIG. 16, the tissue retention system may be adjusted or revised by, at block 618, un-attaching the secondary anchor zone from its anchor location. This may include un-attaching the secondary anchor zone from the anchor pad, or may include peeling the secondary anchor zone from the patient's skin, or an inanimate object, such as a mechanical structure to which it may be attached. Keeping the tension zone taught, the health care provider may grasp the backing of the auxiliary anchor zone and peel it from the adhesive surface of the auxiliary anchor zone. This exposes the adhesive surface which may then be brought into contact against the skin. At block 620, after adhesively adhering the auxiliary anchor zone, the secondary anchor zone may be re-attached as desired.

In addition, the tissue retention system may be a part of a kit. In some implementations, the kit may include a pouch or tray in which a tissue retention belt and an anchor pad may be stored or placed for use. In some implementations, the kit includes one tissue retention belt and two anchor pads. In some implementations, a second pouch or tray (not shown) may be provided within the pouch or tray and may contain therein one or more anchor pads. This may keep the tissue retention belt and pads from attaching to each other during storage or shipping and provides easier access to an attending health care provider. Other configurations of the above are also contemplated.

In some implementations, the kit may be assembled for specific surgical procedures. For example, a child birthing kit may include one or more anchor pads, one or more tissue retention belts, a cotton tip applicator, bulb syringe, pads, gauze, suction tubing, cord clamp, and a Foley catheter. It also may include a drape, table cover, gowns, basins, bowls, laps, absorbent towels, disposal bags, mayo stand cover, Bovie, sterile towels, light handle covers, labels, marking pen, and drapes/pouch, among other items. The kit also may include these following items that may be used during the procedure: a drape, table cover, gowns, 2 basins, laps, 1 disposal bag, needle counter, 1 six inch cotton tip applicator, tray organizer, 1 bulb syringe, 1 mayo stand cover, 1 CSR, wrap×2, Bovie (cauterizing unit), 1 pitcher (1200 ml), sterile towels, 2 pads, 1 gauze 18"×18", 2 light handle covers, 4×4 raytex-10, 1 absorbent towel, 1 blue bowl, suction tubing, labels, 1-CSR poly-back, 2 #20 blades, cord clamp, marking pen, suction equipment, drapes/pouch, Foley catheter. It also may include the physician's preference for sutures, dressing, staples, JP drains. A discussion of an exemplary method and/or additional items that may be included in the kit is provided in U.S. Pat. Nos. 4,880,418, 5,676,672, and 6,102,924, all incorporated herein in their entirety by reference.

In another example, a femoral catheterization kit may include one or more anchor pads, one or more tissue retention belts, a needle sized to puncture the patient's skin and enter the femoral artery, and a flexible hollow tube such as a catheter for threading through the femoral artery. A discussion of an exemplary method and additional items that may be included in the kit is provided in U.S. Pat. No. 4,355,026, incorporated herein in its entirety by reference.

In yet another example, a hysterectomy kit may include one or more anchor pads, one or more tissue retention belts, pads, gauze, cotton tip applicator, suction tubing, and a Foley catheter. It also may include a drape, table cover, a gown, a basin, a bowl, a lap, absorbent towels, disposal bags, mayo stand cover, Bovie, sterile towels, light handle covers, labels, marking pen, drapes/pouch. The kit also may include these following items that may be used during the procedure: a drape, table cover, gowns, 1 mayo stand cover, 2 light handle covers, suction equipment, irrigation, Bovie (cauterizing unit), laps, 1 disposal bag, sponges, absorbent towels. Graspers & dissectors: atraumatic graspers, soft bowel clamps, Maryland dissectors, scissors, needle holders, bipolar forceps and cord, endoloop, tissue morecellator for large uterus. Vaginal instrument table: single tooth tenaculum, Alis graspers, dilators, uterine manipulator, Cohen cannula, speculum, Foley catheter. If doing laparoscopic hysterectomy, the kit also may include 10 mm, 0 degree laparoscope 3 sizes (2-3 mm, 5 mm, 10 mm), and trocars. It may also include the physician preference for suture, dressing, and staples. Other kits and uses also are contemplated.

While providing many advantages over known systems, the tissue retention system disclosed herein is particularly useful on obese patients because it may be effectively used without wrapping around a portion of the patient. For example, it may be entirely applied and used without lifting of limbs, the head, the torso, or legs. It can be applied and used entirely from one side of the patient, such as the patient's front side or the patient's back side. Other advantages, benefits, and uses are described in U.S. Pat. No. 9,408,741, incorporated herein by reference in its entirety.

Applicants note that the procedures disclosed herein are merely exemplary and that the systems and method disclosed herein may be utilized for numerous other medical processes and procedures. Although several selected implementations have been illustrated and described in detail, it will be understood that they are exemplary, and that a variety of substitutions and alterations are possible without departing from the spirit and scope of the present invention, as defined by the following claims.

We claim:

1. A tissue retention belt for maintaining tissue in a position that permits access to a body portion of a patient for a medical procedure, comprising:
   an elongate flexible body having a proximal region, a distal region, and a tension zone between said proximal region and said distal region, said proximal region comprising at a lower surface thereof a first attachment surface having a first attachment feature, said distal region comprising at a lower surface thereof a second attachment surface having a second attachment feature, and said tension zone comprising a non-adhering contact region including a layer of material attached to said tension zone, said layer of material having a non-adhesive lower surface without attachment features configured so as to not adhere to skin of said patient or attach to an inanimate object.

2. The tissue retention belt of claim 1, wherein one of said first attachment feature or said second attachment feature comprises an adhesive.

3. The tissue retention belt of claim 2, wherein said first attachment feature and said second attachment feature each comprise said adhesive.

4. The tissue retention belt of claim 1, wherein one of said first attachment feature or said second attachment feature comprises one of a hook and loop portion of a first hook and loop fastener.

5. The tissue retention belt of claim 4, wherein the other of said first attachment feature or said second attachment feature comprises an adhesive.

6. The tissue retention belt of claim 1, wherein said layer of material is removably attached to said tension zone.

7. The tissue retention belt of claim 1, wherein said elongate flexible body monolithically comprises said proximal region, said distal region, and said tension zone.

8. The tissue retention belt of claim 7, wherein said tension zone is configured to elongate either elastically or in-elastically.

9. The tissue retention belt of claim 1, wherein said tension zone extends the full distance between said proximal region and said distal region.

10. The tissue retention belt of claim 1, wherein said tension zone further comprises an auxiliary zone.

11. The tissue retention belt of claim 10, wherein said auxiliary zone includes a lower surface comprising an auxiliary adhesive.

12. The tissue retention belt of claim 11, wherein said auxiliary zone further comprises a removable backing covering said auxiliary adhesive, said removable backing comprising a non-adhesive surface configured to face skin of said patient.

13. The tissue retention belt of claim 12, wherein said tension zone has a length and said auxiliary zone extends the length of said tension zone.

14. The tissue retention belt of claim 1, wherein said distal region has a first width and said tension zone has a second width substantially the same as said first width.

15. The tissue retention belt of claim 1, wherein said elongate flexible body has a length, said body having a relatively constant width of parallel edges over the length of said elongate flexible body.

16. A tissue retention system, comprising:
a first anchor pad comprising a first adhesive surface, the first adhesive surface being configured to adhere to a first location surface, an opposing first pad attachment surface facing away from the first adhesive surface and including one of a hook and loop portion of a first hook and loop fastener, and a first backing material removably adhered to said first adhesive surface; and
a tissue retention belt in accordance with claim 1, wherein one of said first attachment feature or said second attachment feature comprises the other of a hook and loop portion of said first hook and loop fastener.

17. The tissue retention system of claim 16, further including a second anchor pad comprising a second adhesive surface, the second adhesive surface being configured to adhere to a second location surface, an opposing second pad attachment surface facing away from the second adhesive surface and including one of a hook and loop portion of a a hook and loop fastener, and a second backing material removably adhered to said second adhesive surface.

18. The tissue retention system of claim 16, wherein said tissue retention belt further comprises an auxiliary zone.

19. The tissue retention system of claim 18, wherein said auxiliary zone forms a part of said tension zone of said tissue retention belt.

* * * * *